United States Patent [19]

Bolanos et al.

[11] Patent Number: 5,571,116
[45] Date of Patent: Nov. 5, 1996

[54] NON-INVASIVE TREATMENT OF GASTROESOPHAGEAL REFLUX DISEASE

[75] Inventors: Henry Bolanos, East Norwalk; Jeffrey J. Blewett, Plantsville; Timothy O. Van Leeuwen, Bloomfield, all of Conn.

[73] Assignee: United States Surgical Corporation, Norwalk, Conn.

[21] Appl. No.: 334,614

[22] Filed: Oct. 2, 1994

[51] Int. Cl.⁶ ................................................. A61B 17/04
[52] U.S. Cl. ...................... 606/139; 606/151; 227/175.3; 227/178.1
[58] Field of Search .................................. 606/143, 151, 606/219, 139; 227/19, 175, 180

[56] References Cited

U.S. PATENT DOCUMENTS

| | | |
|---|---|---|
| 1,934,900 | 11/1933 | Wills . |
| 2,541,246 | 2/1951 | Held . |
| 3,261,357 | 7/1966 | Roberts et al. . |
| 3,551,987 | 1/1971 | Wilkinson . |
| 3,717,151 | 2/1973 | Collett . |
| 4,111,206 | 9/1978 | Vishnevsky et al. . |
| 4,310,115 | 1/1982 | Inoue ........................................ 227/19 |
| 4,397,311 | 8/1983 | Kanshin et al. ........................... 227/19 |
| 4,402,444 | 9/1983 | Green ....................................... 227/19 |
| 4,485,817 | 12/1984 | Swiggett ................................ 227/175 |
| 4,573,622 | 3/1986 | Green et al. . |
| 4,607,620 | 8/1986 | Storz ............................................. 128/4 |
| 4,608,965 | 9/1986 | Anspach, Jr. et al. ....................... 128/4 |
| 4,610,383 | 9/1986 | Rothfuss et al. .......................... 227/19 |
| 4,635,638 | 1/1987 | Weintraub et al. ...................... 606/148 |
| 4,655,219 | 4/1987 | Petruzzi . |
| 4,760,848 | 8/1988 | Hasson .................................... 606/148 |
| 4,763,668 | 8/1988 | Macek et al. ........................... 128/751 |
| 4,773,420 | 9/1988 | Green . |
| 4,784,137 | 11/1988 | Kulik et al. ............................... 227/19 |
| 4,863,438 | 9/1989 | Gauderer et al. ....................... 604/247 |
| 4,944,443 | 7/1990 | Oddsen et al. ............................ 227/19 |
| 4,944,732 | 7/1990 | Russo ...................................... 604/247 |
| 4,944,741 | 7/1990 | Hasson .................................... 606/206 |
| 4,982,727 | 1/1991 | Sato ............................................. 128/4 |
| 4,994,079 | 2/1991 | Genese et al. .......................... 606/206 |
| 5,006,106 | 4/1991 | Angelchik ................................. 600/37 |

(List continued on next page.)

FOREIGN PATENT DOCUMENTS

| | | | |
|---|---|---|---|
| 0200723 | 11/1967 | U.S.S.R. ................................. 227/176 |
| 1169625 | 7/1985 | U.S.S.R. ................................. 606/153 |

OTHER PUBLICATIONS

*A Novel Endoscopic Transgastic Fundoplication Procedure for Gastroesophageal Reflux: An Initial Animal Evaluation*, Journal of Laparoendoscopic Surgery, vol. 2, No. 5, 1992.
*Laparoscopic Nissen Fundoplication: Preliminary Report*, Surgical Laparoscopy & Endoscopy, vol. 1, No. 3, pp. 138–143, 1991.
*The Technique of Laparoscopic Nissen Fundoplication*, Surgical Laparoscopy & Endoscopy, vol. 2, No. 3, pp. 265–272, 1992.
*Laparoscopy in Focus*, vol. 1, No. 10/1992.
*Laparoscopic Hill Repair*, Gastrointestinal Endoscopy, vol. 40, No. 2, 1994.
*Surgery for Reflux Disease–Reflections of a Gastroenterologist*, The New England Journal of Medicine, vol. 326, No. 12, Mar. 19, 1992, pp. 825–827.
*Comparison of Medical and Surgical Therapy for Complicated Gastroesophageal Reflux Disease in Veterans*, The New England Journal of Medicine, vol. 326, No. 12, Mar. 19, 1992, pp. 786–792.

Primary Examiner—Gary Jackson

[57] ABSTRACT

Instrumentation for transoral treatment of gastroesophageal reflux disease (GERD) are disclosed. In a preferred embodiment, an instrument includes a remotely operable invagination device for atraumatically approximating the lower esophagus and fundus of the stomach and for invaginating the gastroesophageal junction into the stomach thereby involuting the surrounding fundic wall. The same or a separate instrument includes a remotely operable surgical fastening instrument for fastening together the invaginated lower esophagus and fundic wall. A method of surgically treating GERD is also disclosed.

13 Claims, 23 Drawing Sheets

U.S. PATENT DOCUMENTS

| | | | |
|---|---|---|---|
| 5,007,900 | 4/1991 | Picha et al. | 604/106 |
| 5,015,249 | 5/1991 | Nakao et al. | 606/142 |
| 5,035,248 | 7/1991 | Zinnecker | 128/751 |
| 5,040,715 | 8/1991 | Green et al. | 227/176 |
| 5,042,707 | 8/1991 | Taheri | 606/213 |
| 5,071,430 | 12/1991 | de Salis et al. | 606/219 |
| 5,073,166 | 12/1991 | Parks et al. | 604/93 |
| 5,088,979 | 2/1992 | Filipi et al. | 604/26 |
| 5,099,827 | 3/1992 | Melzer et al. | 128/4 |
| 5,104,394 | 4/1992 | Knoepfler . | |
| 5,141,144 | 8/1992 | Foslien et al. | 227/176 |
| 5,156,608 | 10/1992 | Troidl et al. | 606/142 |
| 5,170,925 | 12/1992 | Madden et al. | 227/175 |
| 5,188,638 | 2/1993 | Tzakis | 606/153 |
| 5,197,649 | 3/1993 | Bessler et al. | 227/19 |
| 5,207,691 | 5/1993 | Nardella | 606/142 |
| 5,254,126 | 10/1993 | Filipi et al. | 606/146 |
| 5,314,436 | 5/1994 | Wilk | 606/153 |
| 5,316,543 | 5/1994 | Eberbach | 600/37 |
| 5,327,914 | 7/1994 | Shlain | 606/220 |
| 5,330,486 | 7/1994 | Wilk | 606/139 |
| 5,368,599 | 11/1994 | Hirsch et al. | 606/139 |
| 5,376,095 | 12/1994 | Ortiz | 606/143 |
| 5,403,326 | 4/1995 | Harrison et al. | 606/139 |

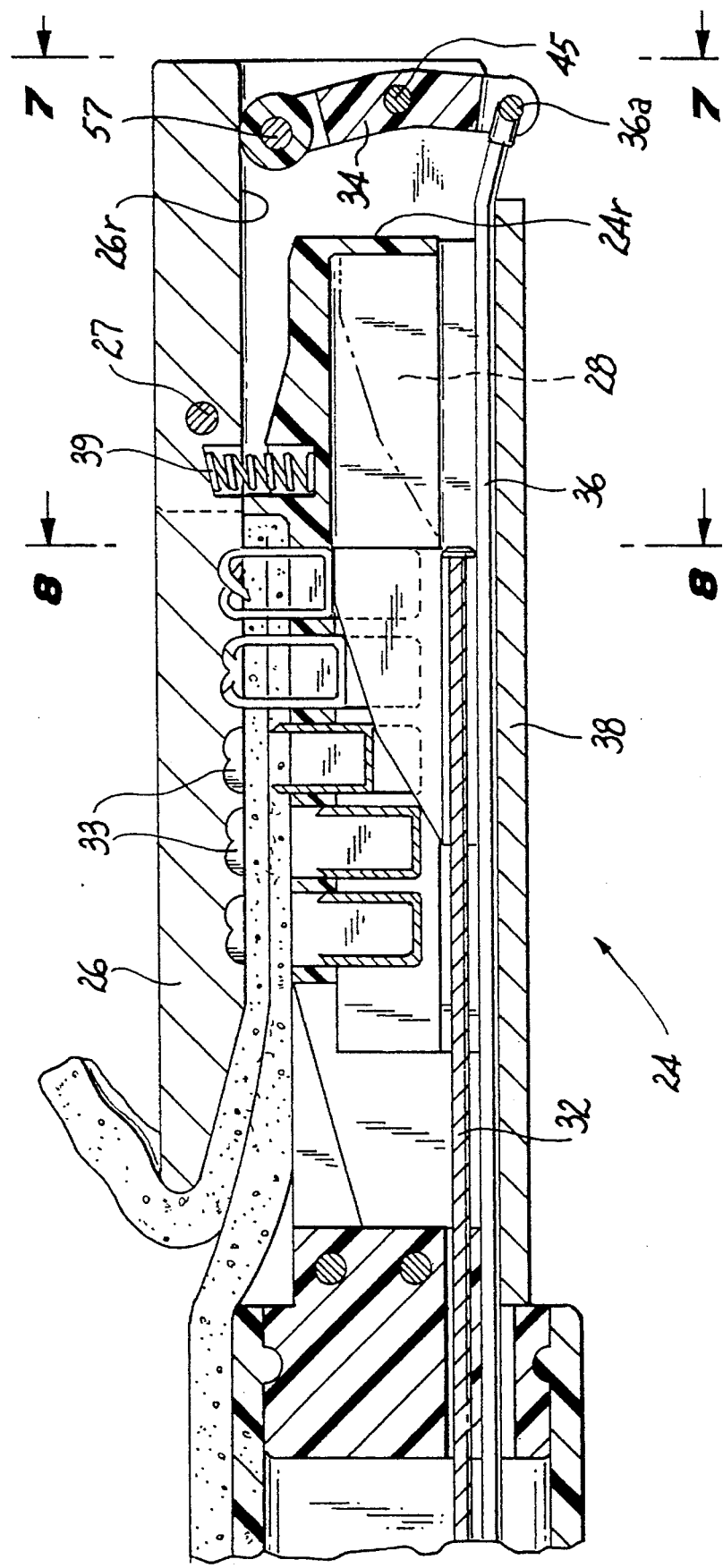

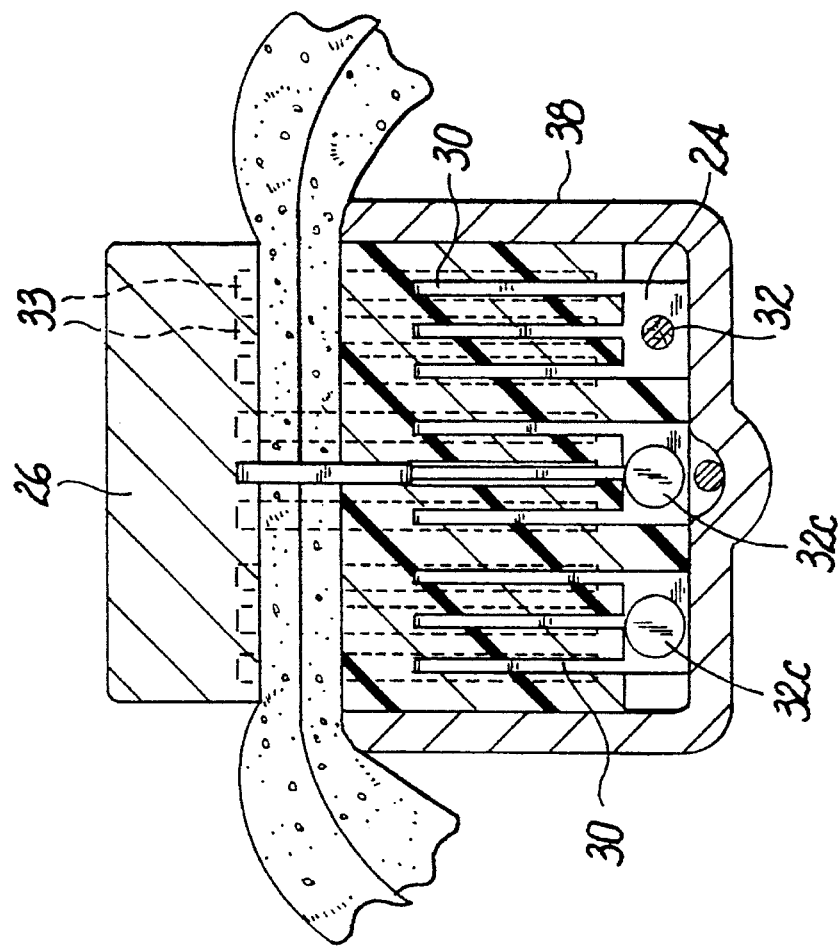
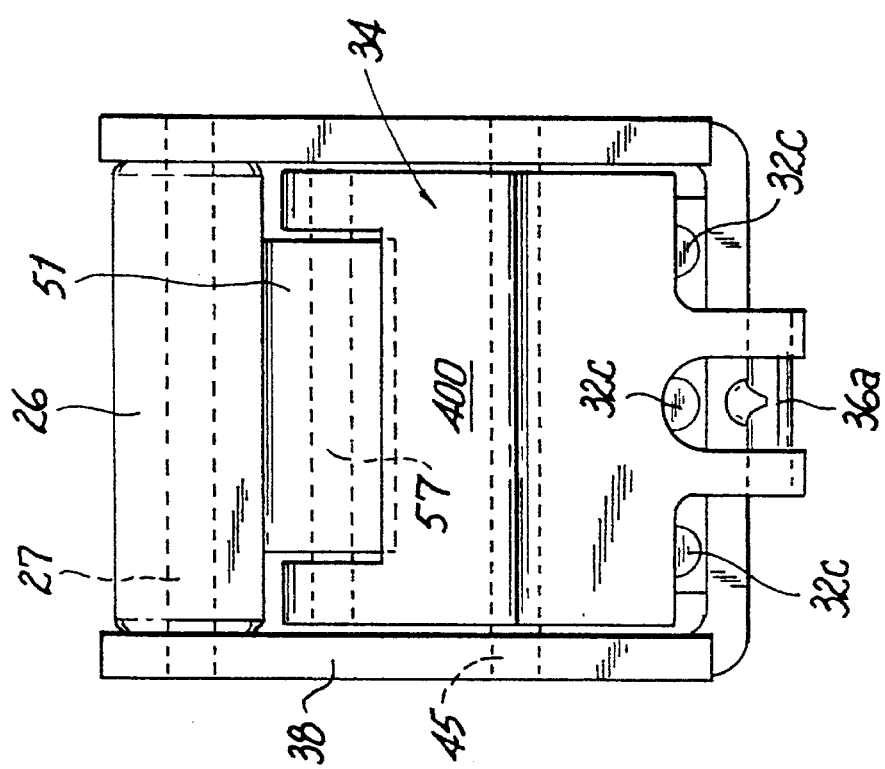

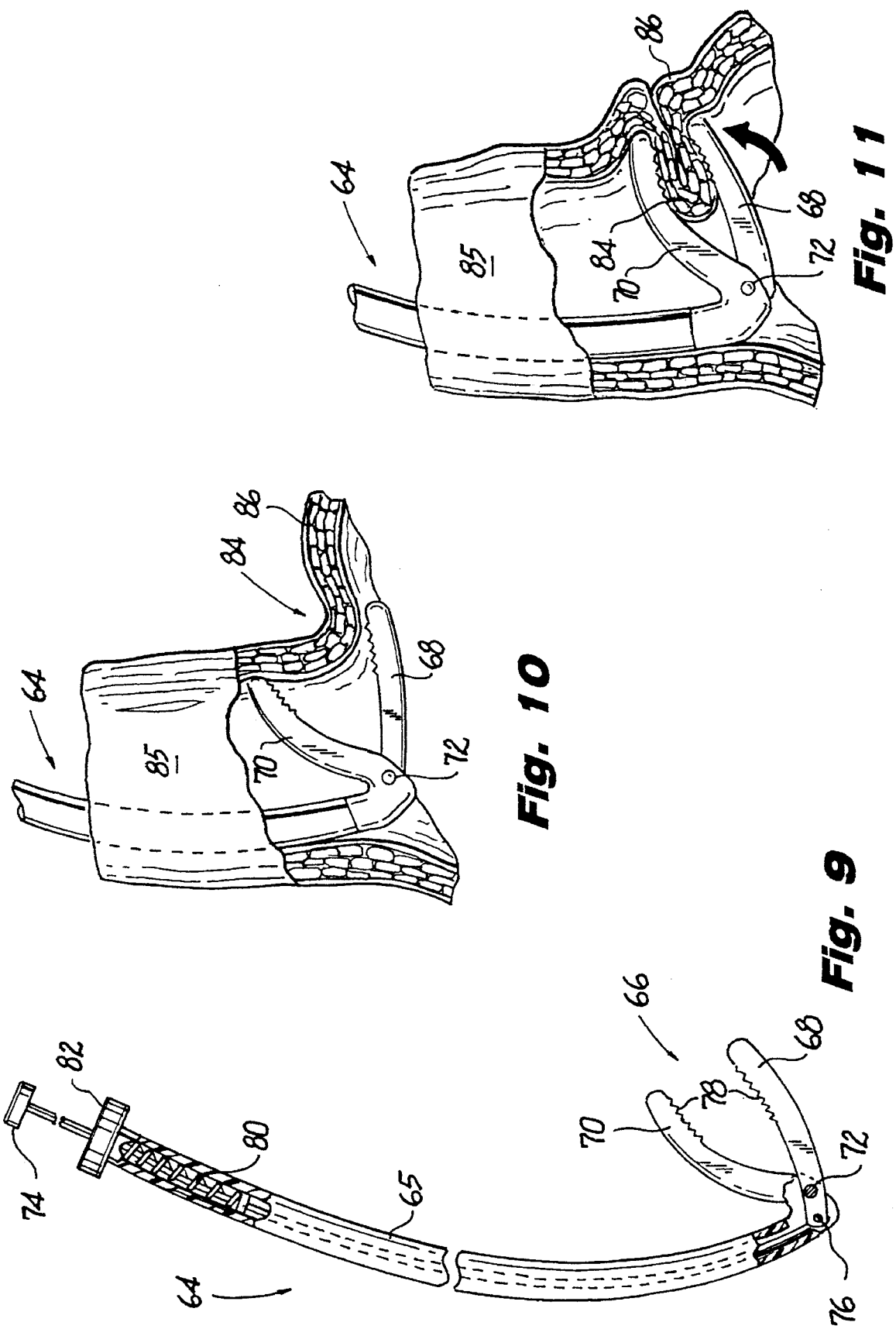

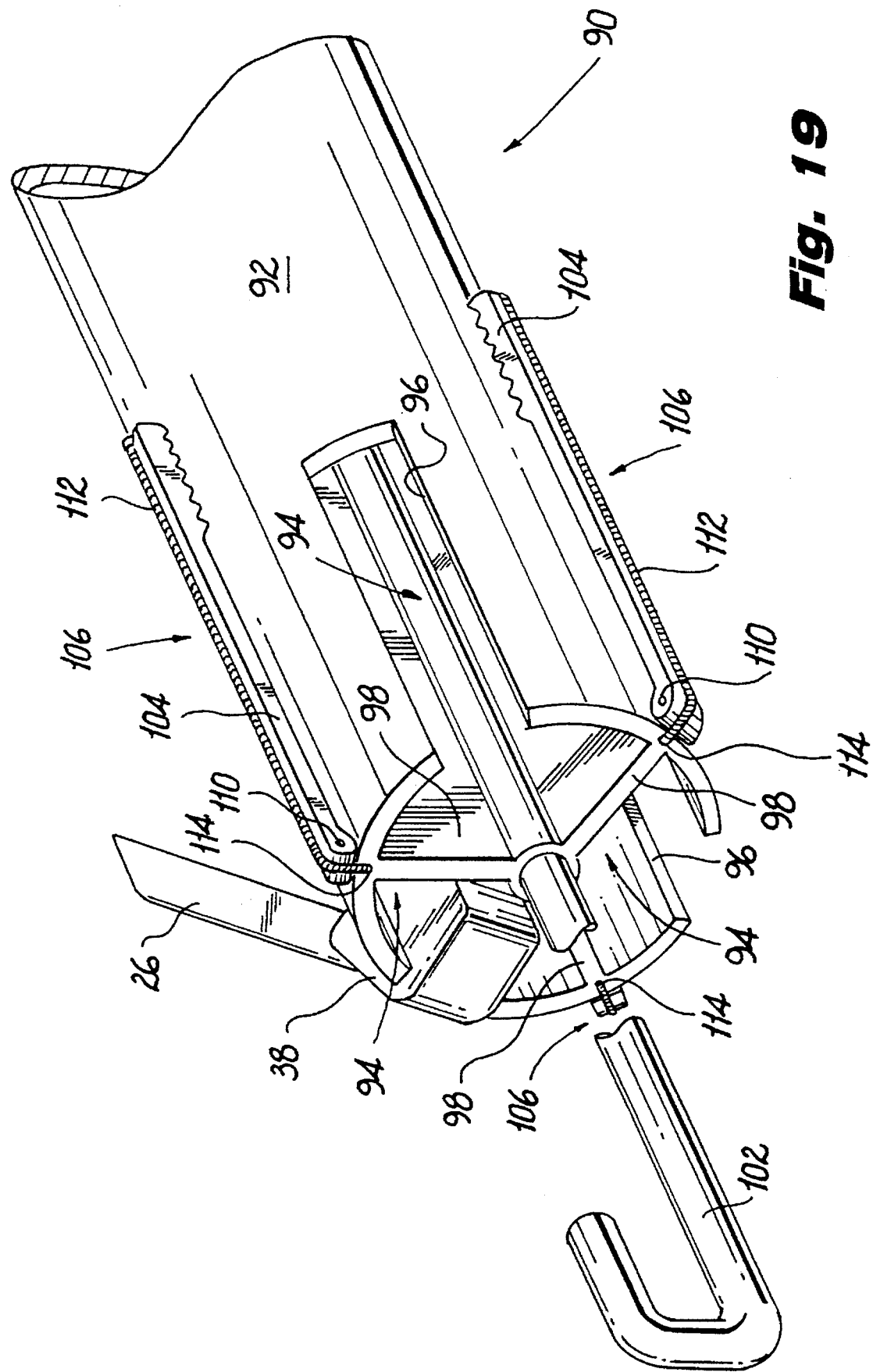

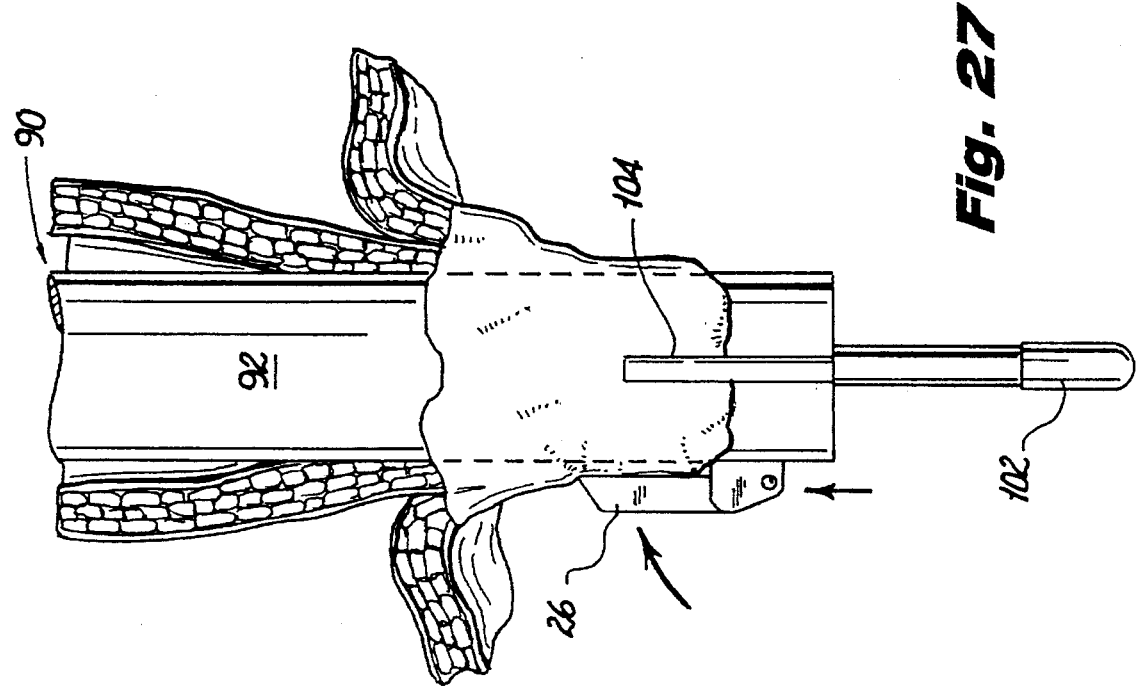
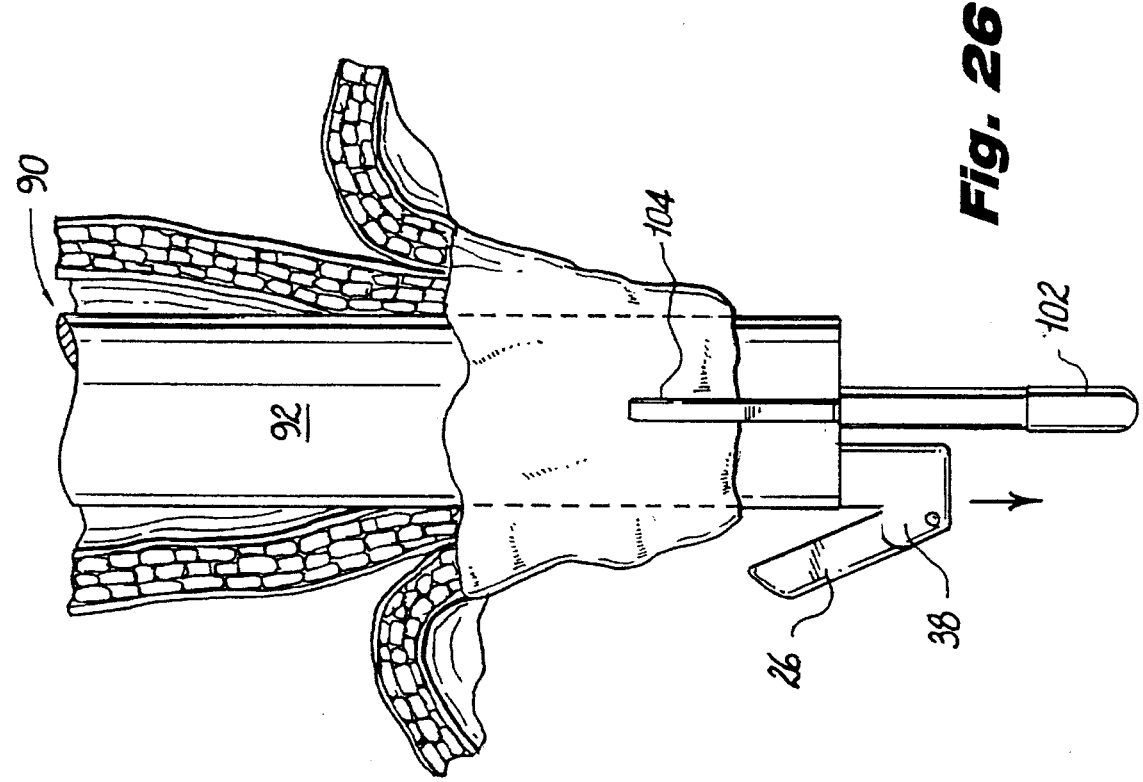

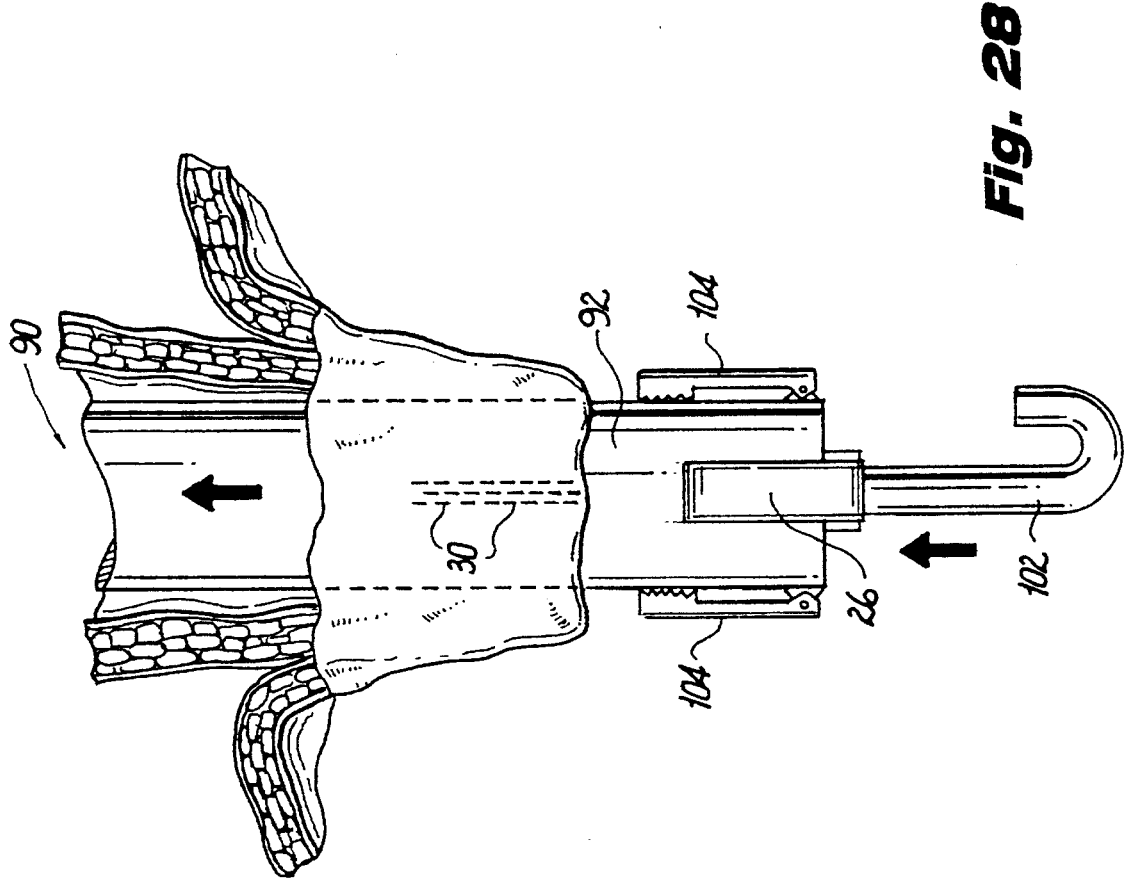

NON-INVASIVE TREATMENT OF GASTROESOPHAGEAL REFLUX DISEASE

BACKGROUND

1. Technical Field

The invention relates to instruments for surgical correction of gastroesophageal reflux disease (GERD) and, more particularly, to surgical instrumentation and methods for performing non-invasive treatment of gastroesophageal reflux disease.

2. Background of the Related Art

Gastroesophageal reflux disease (GERD) is a common gastroesophageal disorder in which stomach contents leak into the lower esophagus due to a dysfunction of the lower esophageal sphincter. As a result, patients suffer numerous symptoms including heartburn, pulmonary disorders, and chest pain. Chronic GERD subjects the esophagus to ulcer formation, esophagitis, and numerous other complications. Advances in drug therapy for GERD include histamine receptor blockers (PEPCID™, ZANTAC™, etc.) which reduce stomach acid secretion and OMEPRAZOLE™ which may completely shut off stomach acid (achlorhydria). Although drugs may provide short term relief, drugs do not address the underlying problem of lower esophageal sphincter dysfunction.

Invasive procedures requiring percutaneous introduction of instrumentation to the operative site exist for the surgical correction of GERD. One such procedure, Nissen fundoplication, involves constructing a new "valve" to support the lower esophageal sphincter by wrapping the gastric fundus around the lower esophagus. Although the operation has a high rate of success. It is a major surgical procedure having the usual risks of abdominal surgery along with the intraoperative risk of perforation of the esophagus or of the cardia.

Efforts to perform Nissen fundoplication by less invasive techniques have resulted in the development of laparoscopic Nissen fundoplication. Laparoscopic Nissen fundoplication, reported by Dallemagne et al. *Surgical Laparoscopy and Endoscopy*, Vol. 1, No. 3, 1991, pp. 138–43 and by Hindler et al. *Surgical Laparoscopy and Endoscopy*, Vol. 2, No. 3, 1992, pp. 265–272, involves essentially the same steps as Nissen fundoplication with the exception that surgical manipulation is performed through a plurality of surgical cannulae introduced using trocars inserted at various position in the abdomen.

Another attempt to perform fundoplication by a less invasive technique is reported in U.S. Pat. No. 5,088,979 (Filipi et al.). In this procedure, an invagination device containing a plurality of needles is inserted transorally into the esophagus with the needles in a retracted position. The needles are extended to engage the esophagus and fold the attached esophagus beyond the gastroesophageal junction. A remotely operated stapling device, introduced percutaneously through an operating channel in the stomach wall, is actuated to fasten the invaginated gastroesophageal junction to the surrounding involuted stomach wall.

Although the above-described surgical procedures all provide the desired effect of supporting or bolstering the lower esophageal sphincter, all require surgical incisions of some kind to introduce the instruments necessary to perform the operation. Those that involve the use of needles within the esophagus also increase the danger of puncturing the esophagus.

A need in the art exists for the treatment of gastroesophageal reflux disease by fundoplication with an instrument system which is non-invasive. Such an instrument system could be used to perform the treatment without the need for any surgical incisions, permitting correction of the lower esophageal defect on an outpatient basis.

SUMMARY

Devices and methods are disclosed for non-invasive treatment of gastroesophageal reflux disease. In one embodiment, a remotely operable invagination device is provided. The device is insertable transorally through the esophagus for atraumatically approximating the lower esophagus and fundus of the stomach and for invaginating the gastroesophageal junction into the stomach. A remotely operable surgical fastening instrument is disclosed which is insertable through the esophagus and capable of fastening the lower esophagus to the fundus of the stomach.

In a preferred embodiment, the fastening instrument is a surgical stapler having an elongated body portion and a cartridge frame positioned at a distal end thereof. At least one cartridge containing a plurality of staples positioned therein is adapted to be received in the cartridge frame. At least one anvil is pivotally connected to the cartridge frame and movable between open and closed positions. The surgical stapler also preferably includes an actuator for moving the anvil between the open and closed positions and a trigger for firing the staples. Other fasteners, such as tacs, two part fasteners, rivots and the like, can also be used to join and/or manipulate tissue.

An invagination device is disclosed which includes an elongated body portion, a first jaw, a second jaw and a pivot member connecting the jaws to a distal end of the elongated body portion. A jaw control mechanism is connected to a proximal end of the elongated body portion and is manipulable to move the jaws between an open and closed position. In a preferred embodiment the jaws are nonlinear, i.e., curved to facilitate grasping of the gastroesophageal junction.

In another embodiment, the invagination device has an endoscopic portion at a distal end thereof. The invagination device includes at least one inner wall, an outer sheath circumferentially attached around the at least one inner wall forming at least one guide channel. The endoscopic portion of the fastener instrument is transorally inserted through the at least one guide channel into the stomach. The invagination device can further include at least one remotely operable and pivotable clamping jaw located at the distal end of the endoscopic portion. The clamping jaw is moveable between an open position and a closed position for atraumatically approximating the lower esophagus and fundus of the stomach, and for invaginating the gastroesophageal junction into the stomach.

A method for treating GERD includes the steps of introducing a remotely operable invagination device transorally through the esophagus and into the stomach; engaging the invagination device with the fundus of the stomach and the lower esophagus; approximating the stomach portion and the esophagus portion to clamp the fundus of the stomach to the lower esophagus; advancing the invagination device distally to invaginate the gastroesophagus junction into the stomach a predetermined distance; and introducing a remotely operable fastening instrument transorally through the esophagus.

The fastening instrument preferably contains a fastener holding member containing at least one fastener and further has at least one anvil jaw including at least one fastener forming depression. Fastener ejector(s) for driving the at least one fastener into contact with the at least one anvil jaw are also provided.

The method further includes the steps of advancing the fastening instrument distally into the stomach; approximating the at least one anvil jaw and the at least one fastener holding member to clamp tissue of the fundus of the stomach to tissue of the lower esophagus together; actuating the fastener ejector(s) to drive the at least one fastener from the fastener holding member through the clamped tissue into contact with the at least one fastener forming depression to secure the tissue together; withdrawing the fastening instrument through the esophagus and out of the patient; withdrawing the invagination device through the esophagus and out of the patient.

In a preferred variation of the method, the fastening step includes placing a line of staples through the clamped tissue a predetermined distance proximal to the invaginated gastroesophageal junction to form a desired size tissue fold distal to the staple line. The fold reduces the inner diameter of esophagus in proximity to the gastroesophageal junction.

In another variation of the method, the stapling step further includes repeating the fastening procedure at least once to create at least one additional fold to further reduce the diameter in proximity to the gastroesophageal junction.

In another preferred variation of the method, an additional step is provided prior to the stapling step, which involves the preconditioning of the tissue to be joined. In another variation of the method, a bolster or pledger is applied to tissue that is weak or perforated. The bolster or pledger is positioned adjacent the clamped tissue, prior to the stapling step, and stapled to the tissue in the stapling step to provide enhanced joining and healing of the stapled tissue.

BRIEF DESCRIPTION OF THE DRAWINGS

FIG. 6B is view similar to that of FIG. 6A illustrating partially fastened tissue.

FIG. 7 is a view taken along lines 7—7 of FIG. 6B.

FIG. 8 is a view taken along lines 8—8 of FIG. 6B.

FIG. 9 is a side view of a preferred embodiment of an invagination device of the present invention.

FIGS. 10–11 are views showing the invagination device of FIG. 9 clamping esophageal and stomach tissue together.

FIG. 19 is a perspective view of an invagination device in accordance with another preferred embodiment of the present invention.

FIG. 26 is a view similar to that of FIG. 25 showing distal movement of a stapling device relative to the invaginated tissue.

FIG. 27 is a view similar to that of FIG. 26 showing the stapling device engaging the invaginated tissue.

FIG. 28 is a view similar to that of FIG. 27 showing the invaginated tissue after having been stapled.

DETAILED DESCRIPTION OF PREFERRED EMBODIMENTS

Figure 1:
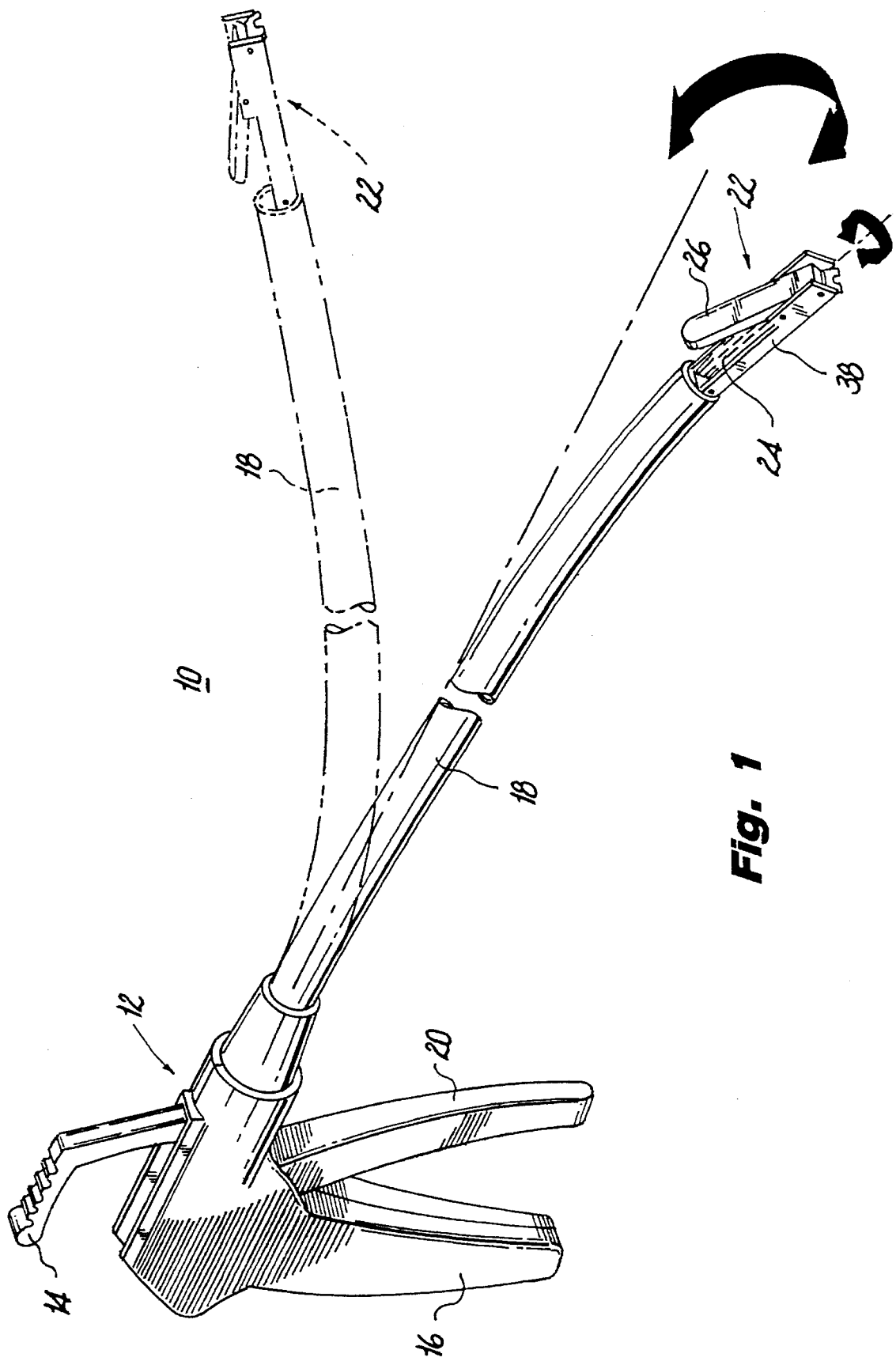
FIG. 1 is a perspective view of a fastening instrument in accordance with a preferred embodiment of the present invention.
Figure 2C:
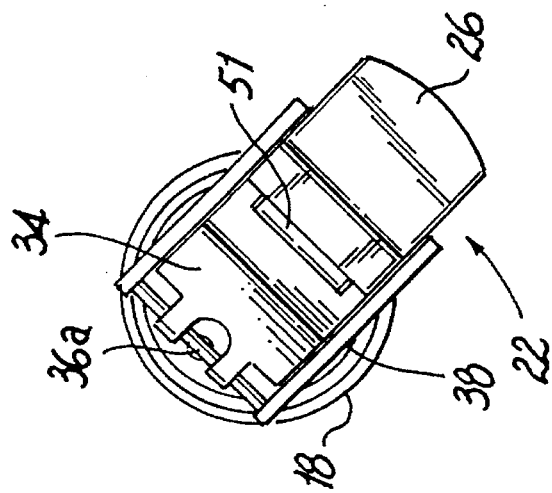
FIG. 2A–2C are frontal views of the fastening instrument of FIG. 1 at various orientations.
Figure 2B:
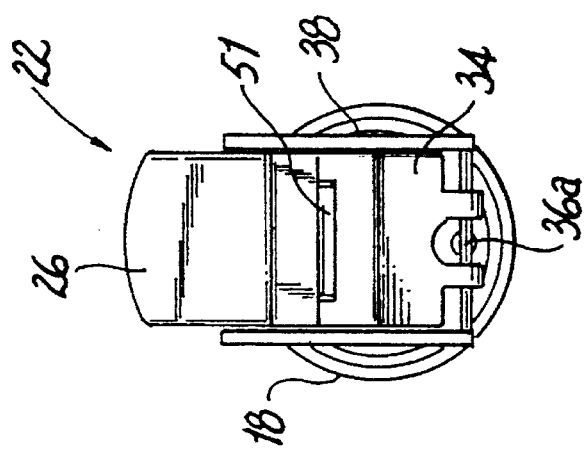
Figure 2A:
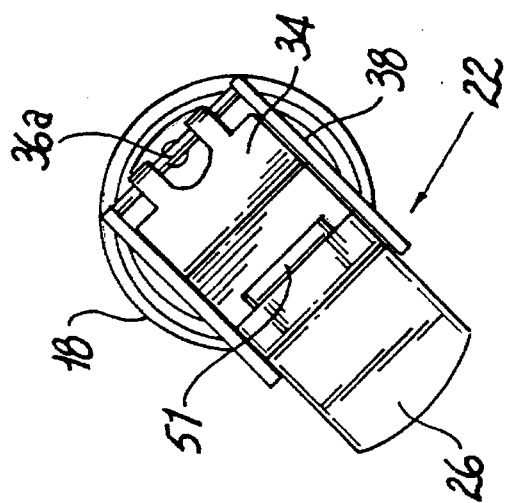
Figure 3:
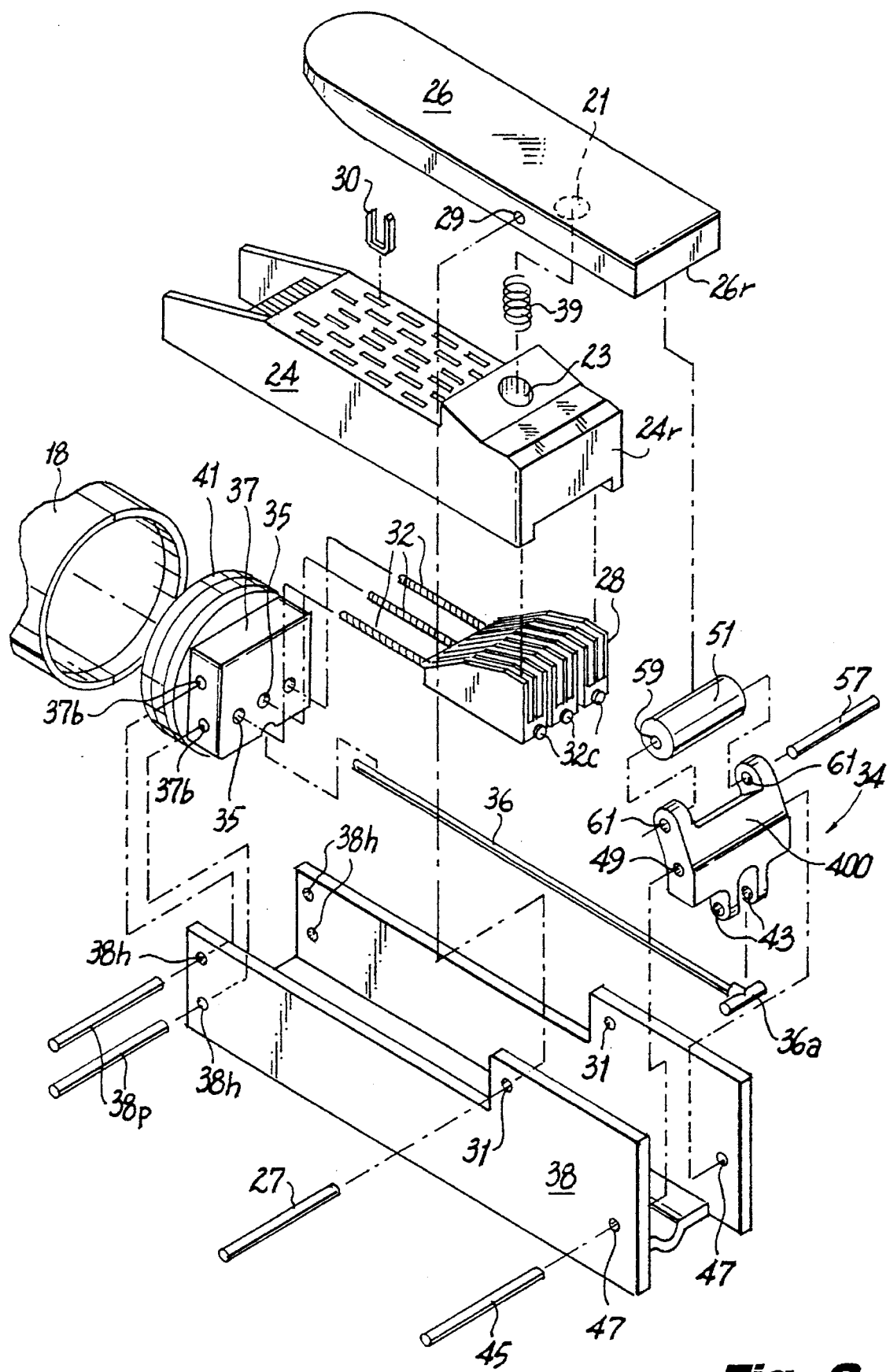
FIG. 3 is a an exploded perspective view illustrating the distal stapling assembly of the fastening instrument of FIG. 1.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

A preferred embodiment of the apparatus of the present invention will now be described with reference to FIGS. 1–4 which illustrate fastening instrument 10. Fastening instrument 10 includes a frame 12 supporting an elongated flexible portion 18, anvil control lever 14, stationary handgrip 16, and movable trigger 20. Elongated flexible portion 18 defines a longitudinal axis and has sufficient length to reach the operative site, in this case, transorally to the gastroesophageal junction. At the distal end of elongated portion 18 is fastening assembly 22. Fastening assembly 22 includes staple carrying cartridge 24, disposed in cartridge frame 38, and anvil 26, pivotally connected to the distal end cartridge frame 38. The proximal end of cartridge frame 38 is secured to the distal end of elongated portion 18.

Turning to fastening assembly 22, with reference to FIGS. 3–4 and 6–8, staple ejectors 28 are provided to eject staples 30 contained in staple cartridge 24. Staple ejectors 28 are linked to moveable trigger 20 by elongate firing cables or members 32 which are secured at one end to staple ejectors 28 by cable caps 32c, and which extend through bores 35 in block member 37 and collar member 41 and are secured at the other end to pulleys 48 in frame 12. Staple ejectors 28 are linked to moveable trigger 20 such that proximal movement of the trigger causes staple ejectors 28 to be moved proximally. Proximal movement of staple ejectors 28 drive staples 30 from staple cartridge 24 into anvil forming recesses 33, as is known in the art of surgical stapling.

Cartridge frame 38 is secured to block member 37 by pins 38p which pass through bores 37b in block member 37 and holes 38h in cartridge frame 38. Collar member 41 is secured to both block member 37 and to the distal end of elongate portion 18 by any suitable means, i.e., friction fit, weld, glue, pins or the like.

With reference to FIGS. 1, 3 and 6A–6B, an anvil control mechanism is disclosed. Anvil control lever 14 is linked to roller assembly 34 by means of wire or rod 36 which terminates in "T" portion 36a. "T" portion 36a is positioned through holes 43 in anvil moving member 400 of roller assembly 34. Pivot pin 45 passes through holes 47 in cartridge frame 38 and bore 49 in pivoting member 400 to pivotally secure anvil moving member 400 to cartridge frame 38. Roller member 51 is rotatably connected to anvil moving member 400 by roller pin 57 which passes through roller bore 59 and roller holes 61. Anvil 26 is pivotally connected to cartridge frame 38 by pivot pin 27, which passes through anvil bore 29 and frame holes 31. Spring member 39 is provided to bias anvil 26 in an open position in which the staple deforming surface of anvil 26 and the tissue contacting surface of staple carrying cartridge 24 are not in alignment. Spring member 39 is affixed at one end to face portions 23 of staple carrying cartridge 24 and at the other end to face portion 21 of anvil 26.

To close anvil 26, control lever 14 is moved towards frame 12 which pulls rod 36 proximally, thereby pivoting roller assembly 34 about connecting pin 45. As roller assembly 34 pivots, roller member 51 is brought into contact with roller surface 26r of anvil 26. Further movement of control lever 14 further pivots roller assembly 34 causing anvil 26 to pivot about pivot pin 27 until the staple deforming surface of anvil 26 is adjacent the tissue contacting surface of staple carrying cartridge 24. In the closed position, roller assembly 34 is over-centered and provides sufficient force to hold anvil 26 in place during firing of the staples. To open the anvil, control lever 14 is opened to cause roller member 51 of roller assembly 34 to disengage the anvil. Spring 39 facilities opening.

Figure 4:
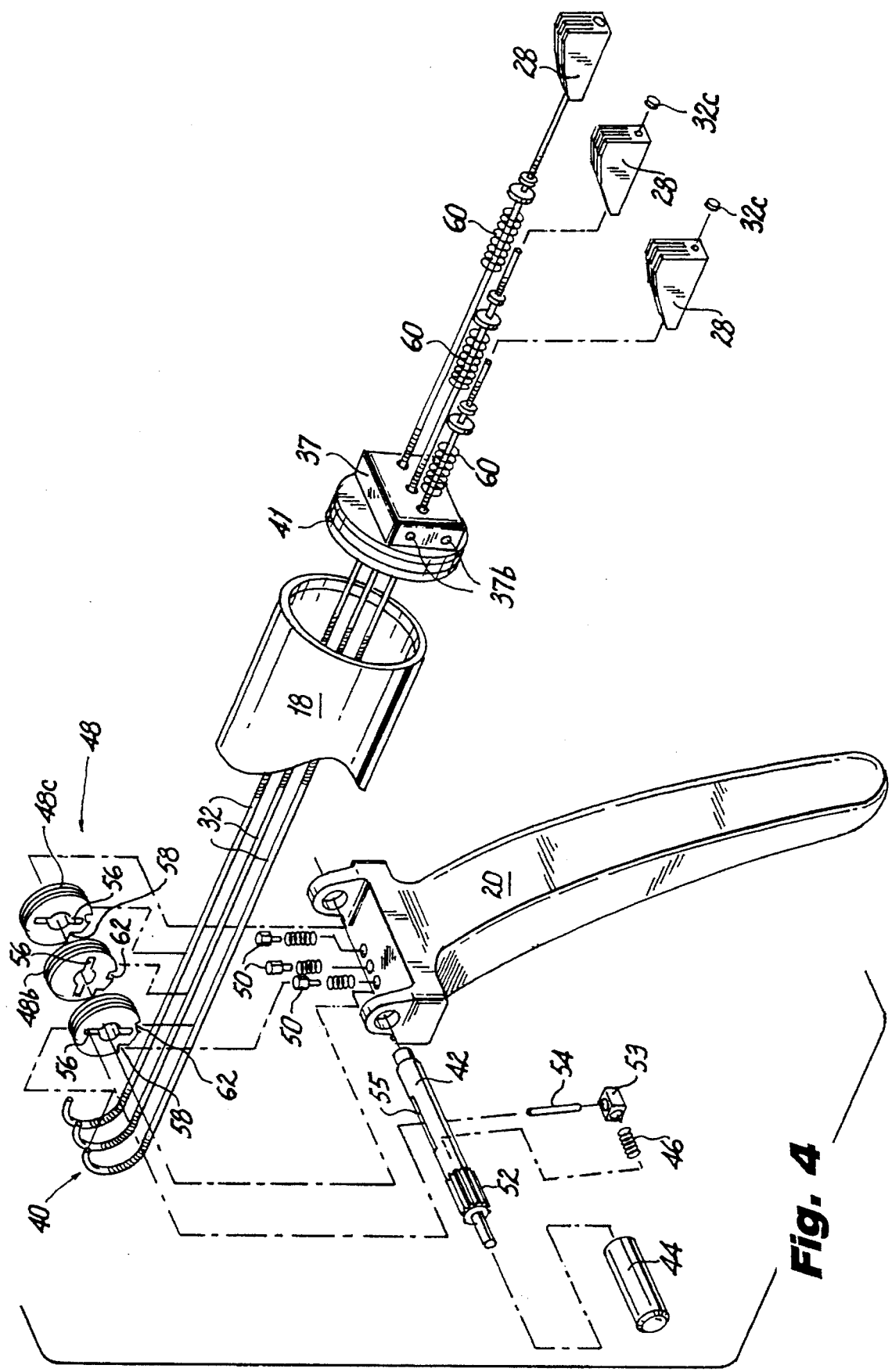
FIG. 4 is an exploded perspective view illustrating a clutch assembly in accordance with a preferred embodiment of the present invention.

A preferred embodiment for firing the instrument is shown in FIG. 4. Clutch mechanism 40 is provided for permitting trigger 20 to sequentially move individual staple ejectors 28. Clutch mechanism 40 includes drive shaft 42, clutch member 44, compression spring 46, keyed drive pulleys 48a–48c and spring fingers 50. Clutch member 44, pressed into trigger 20, is configured with internal ratcheting, not shown, which engage grooves 52 of drive shaft 42 in a manner which permits free distal movement of trigger 20, and corresponding counterclockwise movement of clutch member 44, about drive shaft 42, when trigger 20 is moved proximally, i.e., fired. Proximal movement of trigger 20, corresponding to clockwise movement of clutch member 44, causes locking of clutch member 44 with grooves 52 of drive shaft 42 and clockwise movement of drive shaft 42.

Drive shaft 42 passes through drive pulleys 48a–48c. Sleeve 53, having pin 54 configured for placement within key slots 56 of keyed drive pulleys 48a–48c, is disposed within slot 55 of drive shaft 42. Spring 46 biases pin 54 and sleeve 53 laterally within slot 55. Keyed drive pulleys 48a and 48c are positioned such that their respective key slots 56 are 90° off-set from one another. Resting indents 58 of keyed drive pulleys 48 receive spring fingers 50 and are provided to maintain alignment of the keyed drive pulleys 48 which are spring biased in a counter clockwise direction by means of cable springs 60.

At an initial resting position, trigger 20 is at a distal position and pin 54 is in key slot 56 of first keyed drive pulley 48a. Proximal movement of trigger 20 rotates first keyed pulley 48a 90° clockwise into a fired position. Rotation of the keyed pulleys causes cables 32 to pull one of the ejectors 28 proximally, thereby firing at least one of the rows of staples. Therefore, after the first firing of trigger 20, at least one row of staples is ejected while at least another row of staples remains in the cartridge. After trigger 20 completes the firing stroke, spring finger 50 locks first keyed drive pulley 48a into its fired position by means of engagement of spring finger 50 with locking indent 62. In this fired position, key slot 56 of first keyed drive pulley 48a is moved into alignment with key slot 56 of second keyed drive pulley 48b. This alignment allows spring 46 to bias sleeve 53 and pin 54 into key slot 56 of second keyed drive pulley 48b. Trigger 20, as previously described, is permitted to freely return to its distal position allowing the above described operation to be repeated twice more to sequentially fire the remaining staples. While three ejectors are shown, it is within the scope of the invention to have one or more ejectors be actuated by trigger 20.

An alternative clutch and drive mechanism (not shown) can include a roller clutch in place of clutch 44, pin 54 being integral with shaft 42 and a spring to laterally bias shaft 42 during firing. In this embodiment, the roller clutch would provide clockwise rotation of shaft 42 during firing and allow trigger 20 to return without rotating shaft 42.

Figures 5A, 5B:
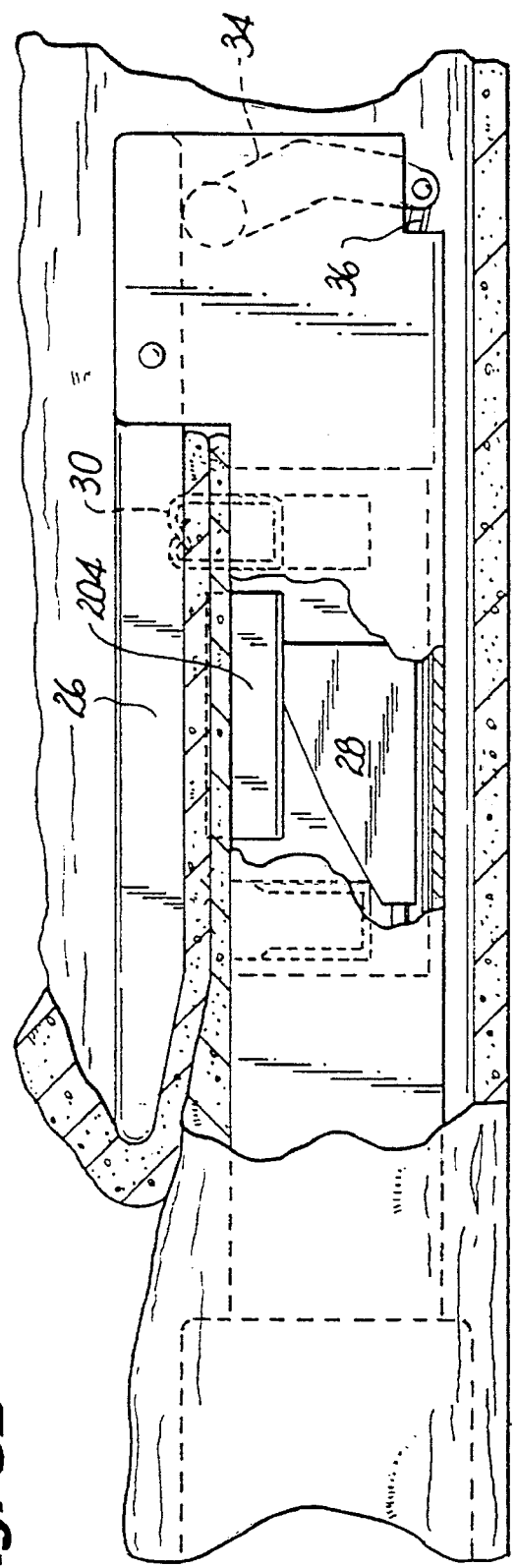
FIG. 5A is a perspective view illustrating a staple cartridge of a preferred embodiment of the present invention.
FIG. 5B is a view of the cartridge of FIG. 5A illustrating a knife being driven through a slot in the cartridge.
Figure 5C:
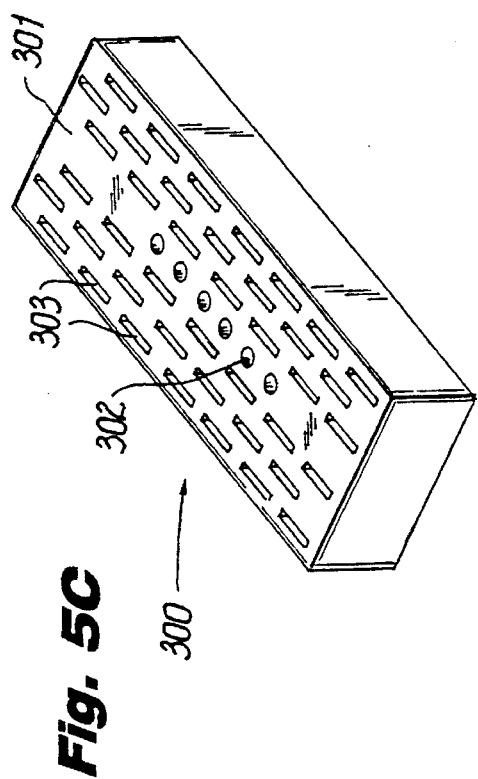
FIG. 5C is a perspective view illustrating a staple cartridge of a preferred embodiment of the present invention.

Turning to staple cartridges suitable for use in the fastening assemblies described hereinabove, preferred embodiments are shown in FIG. 5A and 5C. It may be desirable to promote the joining of and the healing of tissue by preconditioning or traumatizing the tissue to be stapled. The preconditioning or traumatizing can include the roughening or abrading of the tissue to provoke an inflammatory response from the tissue which has been found to promote the joining and healing of the tissue. Accordingly, in FIG. 5A, replaceable staple cartridge 200 is provided for placement into cartridge frame 38 of fastening instrument 10. Staple cartridge 200 has tissue containing surface 201, knife slot 202, staple receiving slots 203 and knife blade 204. When staple ejector 28 is drawn longitudinally through cartridge 200 (FIG. 5B), knife blade 204 is cammed vertically through slot 202 from a first position below tissue contacting surface 201 to a second position above the tissue contacting surface, thereby causing an inflammatory response.

Figure 5D:
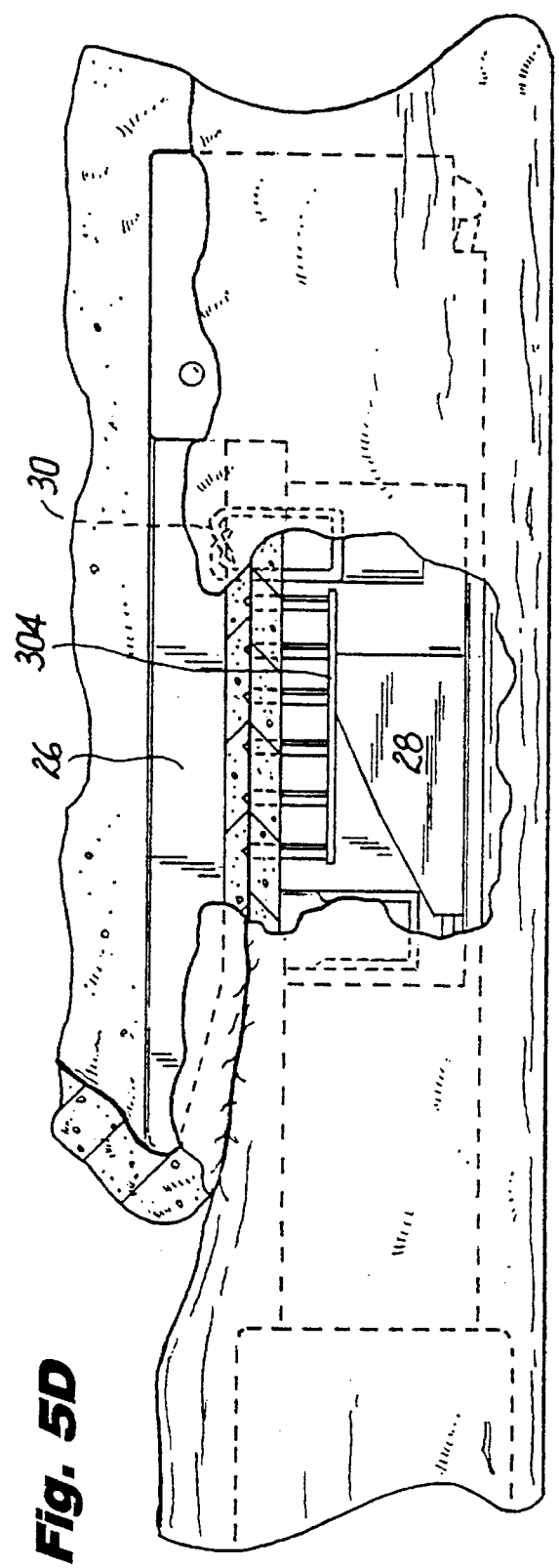
FIG. 5D is a view taken of the cartridge of FIG. 5C illustrating dart members being driven through perforations in the cartridge.
Figure 6A:
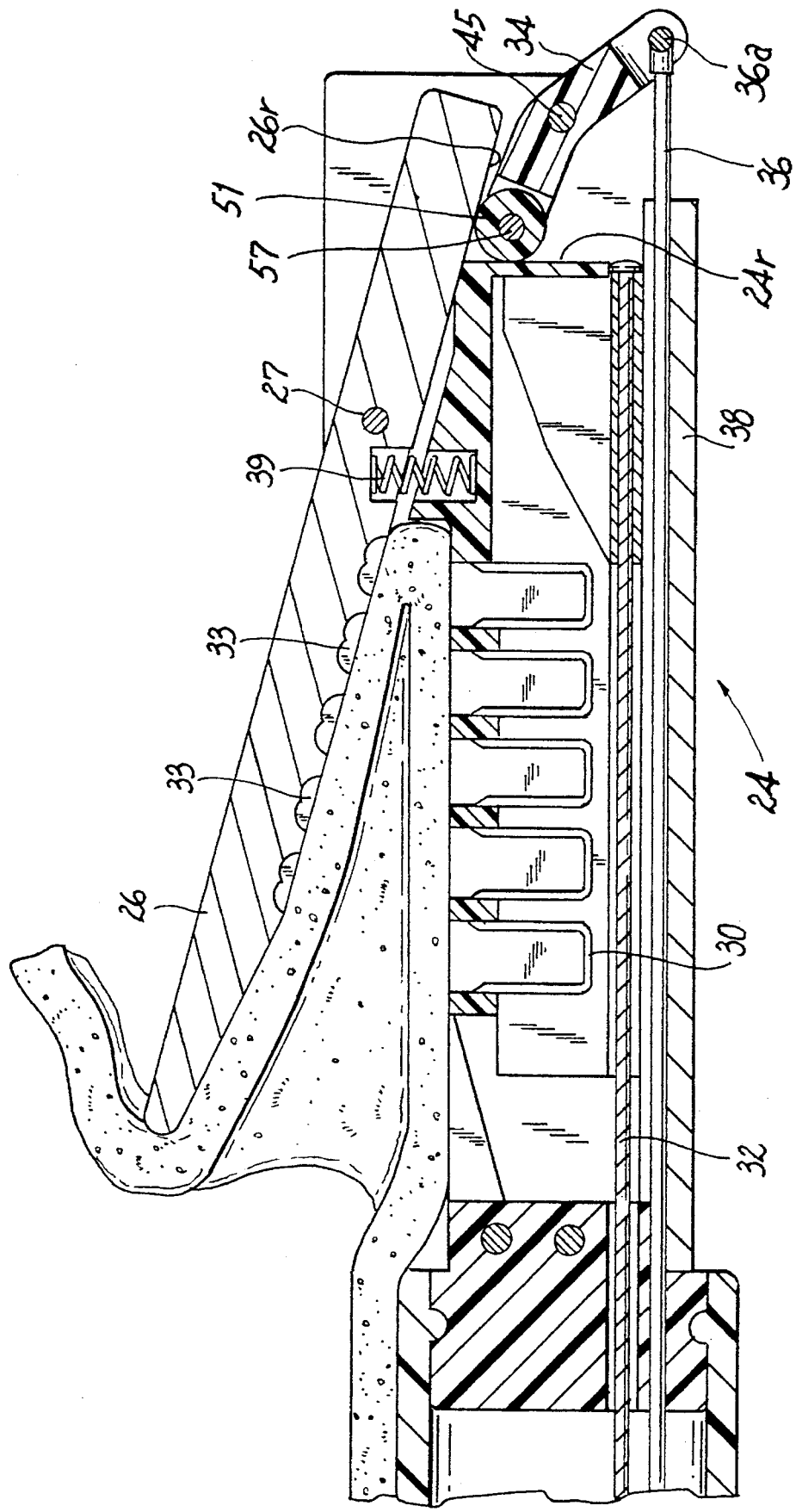
FIG. 6A is a partial side view of the distal stapling assembly of FIG. 1 with the anvil in an open position.
Figure 13:
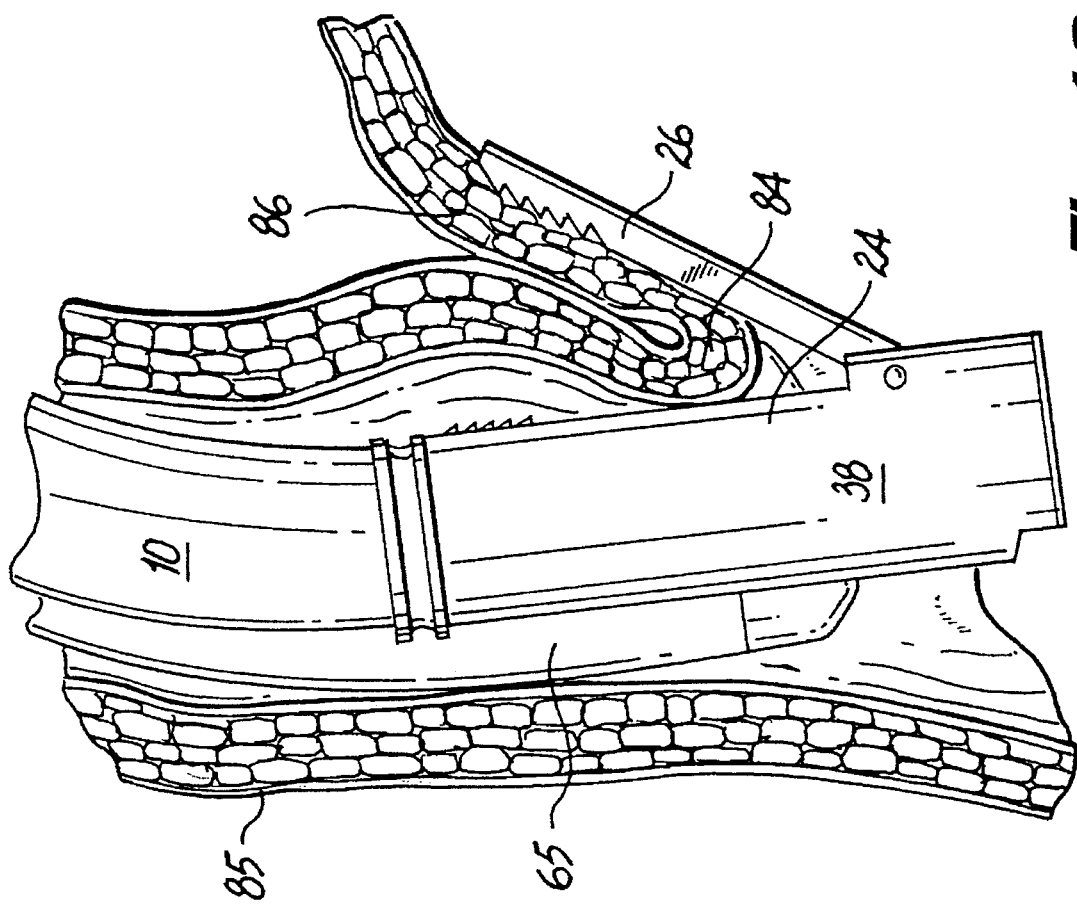
FIG. 13 is a view similar to that of FIG. 12 showing the stapling device of FIG. 1 in a partially open position at the gastroesophageal junction.

In another preferred embodiment, as shown in FIGS. 5C and 5D, staple cartridge 300 has tissue contacting surface 301, staple receiving slots 303 and a plurality of perforation holes 302 to permit passage of dart members 304 therethrough to precondition the tissue to be joined. Dart members are urged vertically during firing in a manner similar to that described with respect to knife blade 204. While the staple cartridges described have inflammatory response mechanisms, such mechanisms are not necessarily required. In addition, the staples need not be disposed in "cartridges" but can be directly associated with frame 38.

An invagination device is disclosed in FIGS. 9–12. Referring to FIG. 9, invagination device 64 includes flexible body portion 65 and remotely operable jaw member 68 pivotably connected to fixed jaw member 70 by pivot pin 72. Jaw moving member 74 passes through body portion 65 and is pivotally secured to jaw member 68 at position 76 such that distal movement of jaw control member 74 causes jaw member 68 to pivot about pivot pin 72. Preferably, grip enhancing surfaces 78 are provided on jaw members 68 and 70 to facilitate the grasping of tissue therebetween. Jaw control member 74 is biased proximally by spring 80 and can be locked in any position by locking member 82. In one embodiment, locking member 82 is a compression collar.

Figure 12:
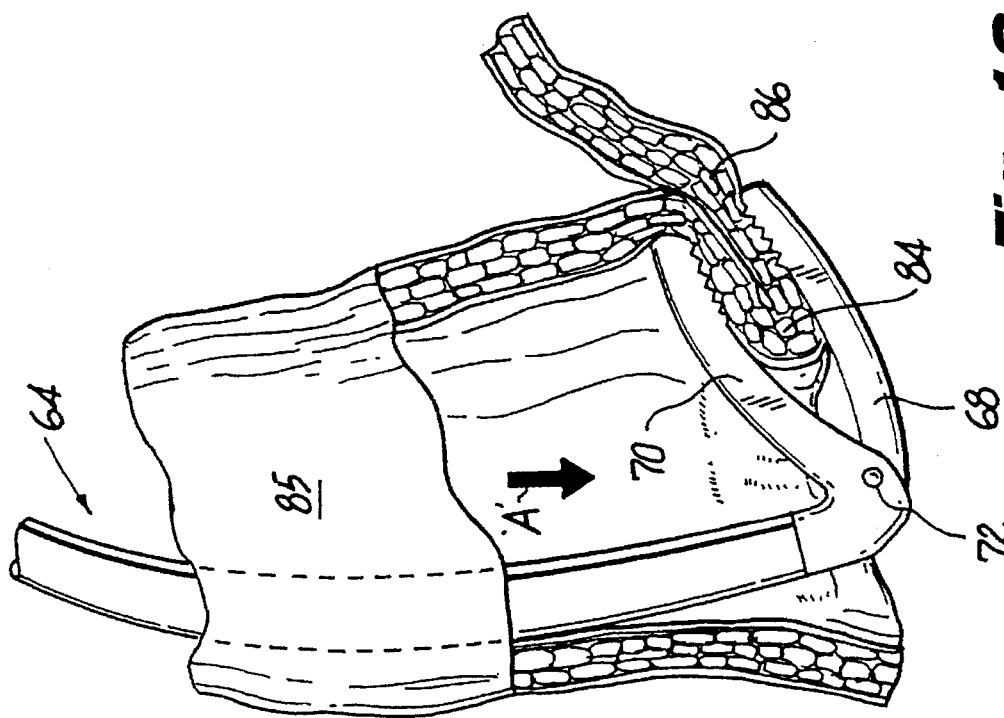
FIG. 12 is a side view of the invagination device of FIG. 9 illustrating the gastroesophageal junction being invaginated into the stomach.

A preferred method of carrying out a minimally invasive GERD repair will now be described with reference to FIGS. 10–18. Invagination device 64 is transorally inserted through the esophagus into the stomach and positioned at gastroesophageal junction 84. Referring to FIGS. 10–11, operable jaw member 68 and fixed jaw member 70 are manipulated to engage and firmly clamp gastroesophageal junction 84. Gastroesophageal junction 84 is located at the union of the distal end of esophagus 85 with fundic wall 86. Referring to FIG. 12, once so engaged, invagination device 64 is advanced distally into the stomach, as indicated by arrow "A", this movement "invaginates" gastroesophageal junction 84 and "involutes" surrounding fundic wall 86. Fastening instrument 10 is then transorally introduced into the stomach to staple fundic wall 86 to invaginated gastroesophageal junction 84. Optionally, a tube of sufficient diameter can be initially inserted into the esophagus and left in place until the procedure is complete. Such a tube facilitates passage of instruments and shields the esophagus.

Figure 15:
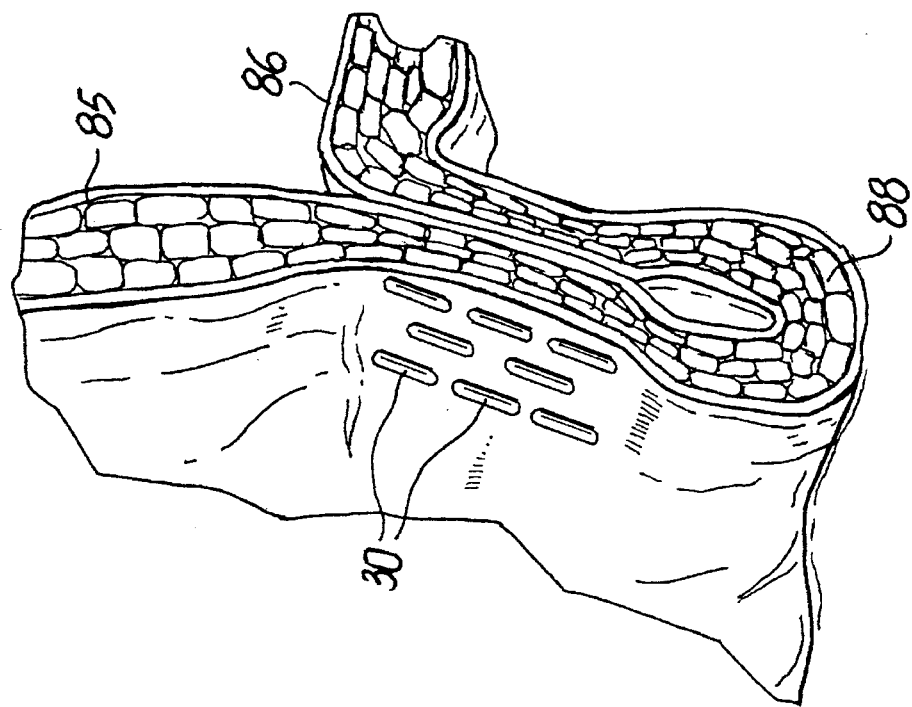
FIG. 15 is an enlarged cross-sectional view illustrating a stapled gastroesophageal junction and tissue fold.
Figure 14:
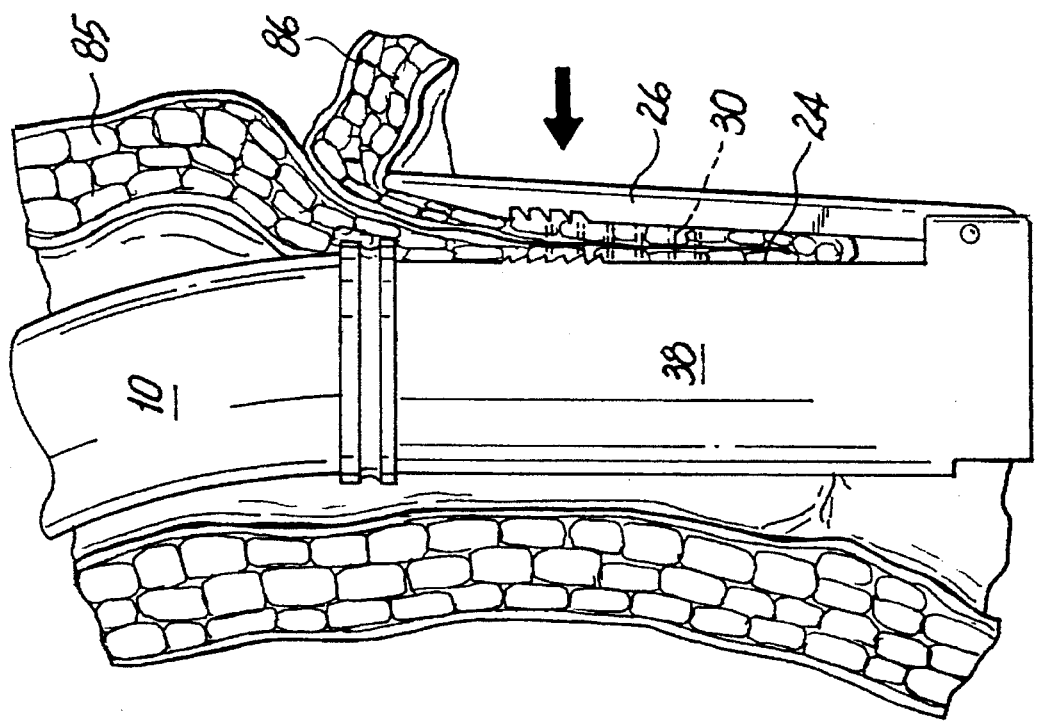
FIG. 14 is a view similar to that of FIG. 13 showing the stapling device engaging and clamping the gastroesophageal junction.
Figure 17:
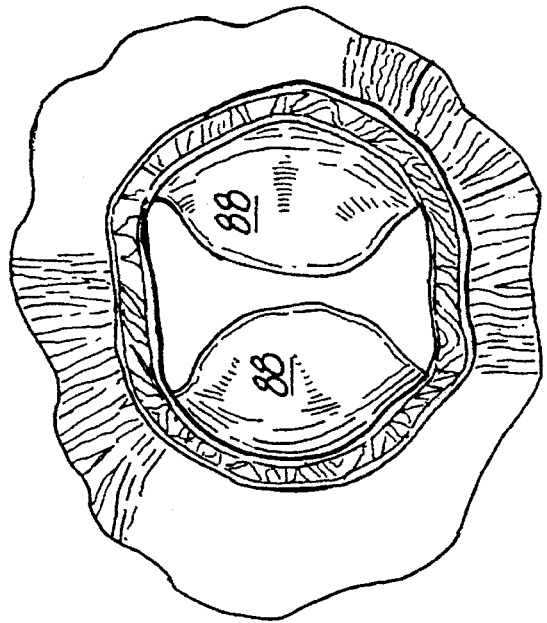
FIG. 17 is a view similar to that of FIG. 16 illustrating two tissue folds.
Figure 18:
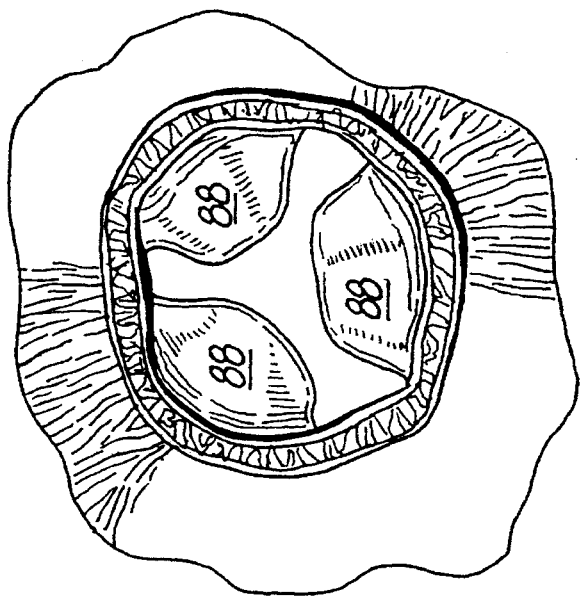
FIG. 18 is a view similar to that of FIG. 16 illustrating three tissue folds.
Figure 16:
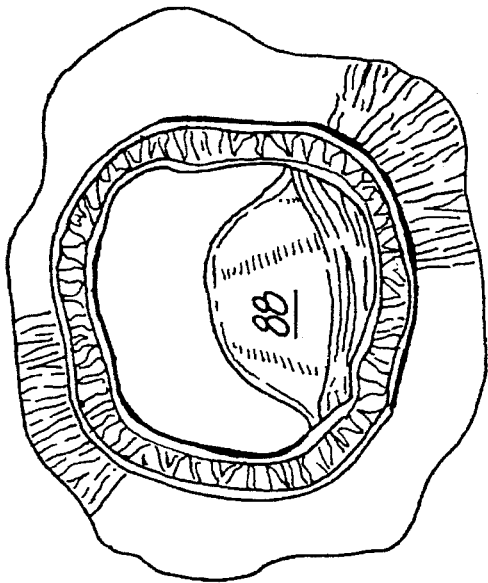
FIG. 16 is a top cross-sectional view of the esophagus illustrating a single tissue fold at the gastroesophageal junction.

Referring to FIGS. 1 and 13–18, anvil 26 of fastening instrument 10 is manipulated to engage clamped invaginated gastroesophageal junction 84 and fundic wall 86. Anvil control lever 14 is rotated to firmly clamp gastroesophageal junction 84 and fundic wall 86 between anvil 26 and cartridge 24. Once clamped, trigger 20 is moved proximally causing at least one row of staples 30 to be driven out from cartridge 24, through clamped gastroesophageal junction 84 and fundic wall 86, into contact with anvil 26. Referring to FIGS. 15–16, staples 30, driven into anvil forming recesses 33 of anvil 26 (FIG. 5), are deformed to securely fasten gastroesophageal junction 84 to fundic wall 86, thereby creating tissue fold 88. FIGS. 17 and 18 illustrate additional tissue folds 88 created by repeating the above described process. While two or three rows of staples should be sufficient to hold formed tissue fold(s) 88 in place to maintain their functionality, fewer or more rows may be desirable. As illustrated in FIGS. 14–15, in order to create tissue fold 88 staple carrying cartridge 24 is configured such that staples contained therein are not applied to the distal most portions of invaginated gastroesophageal junction 84 and fundic wall 86.

As an alternative or in addition to preconditioning, it may be desirable to employ the use of a bolster to further promote joining and healing of tissue. The tissue to be joined may have experienced negative symptoms associated with GERD that inhibit the joining and or healing of the tissue. Accordingly, a bolster may be positioned around the clamped invaginated gastroesophageal junction 84 and fundic wall 86. The bolster can then be stapled to the invaginated tissue to provide enhanced joining and healing of the stapled tissue.

Another embodiment of an invagination device is shown in FIG. 19. Invagination device 90 includes body portion 92 and inner anvil channels 94, terminating in stapler guide slots 96. Stapler guide channels 94 are formed by the intersection of walls 98 with one another which gives structural support and rigidity to the instrument as well as performing a guiding function. The number of stapler guide channels can correspond to the number of gastroesophageal folds desired. For example, when desiring three folds of staples spaced 120 degrees apart (FIG. 18), three stapler guide channels are formed in the invagination device.

Advantageously, the provision of plural stapler guide channels permits the user to insert an additional instrument within one of the guide channels not being occupied by a stapler. Such an additional instrument could take the form of forceps, a retraction instrument, or similar tissue manipulating instruments which may assist the user in performing the fundoplication. A coaxial channel 100 permits passage of endoscope 102 down the interior of invagination device 90 to facilitate observation of the fundoplication procedure without interfering with the other instrumentation.

Figure 20:
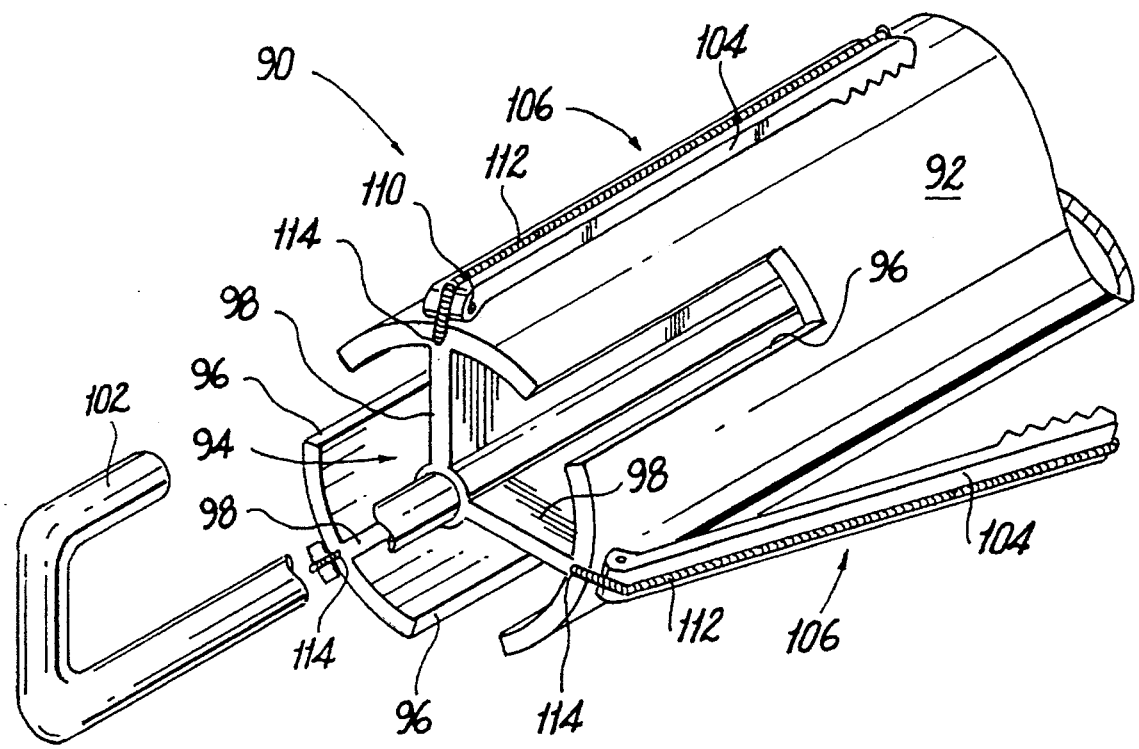
FIG. 20 is a view of the invagination device of FIG. 19 with the arms partially open.

Invagination device 90 can be provided with a plurality of independently actuable tissue clamping members 104 to clamp esophageal and gastric tissue together adjacent the gastroesophageal junction. As best seen in FIG. 20, clamping member 104 includes a forceps-like arm 106, optionally provided with a grip enhancing surface 108 to grip tissue. Clamping member 104 is pivotally mounted to body portion 92 by means of pivot pin 110.

Referring to FIGS. 19 and 20, cables 112 enable the user to open arms 106 to capture tissue between grip enhancing surface 108 and body portion 92. Cables 112 extend through apertures 114 along the outer surface of arms 106 and around arm heads 116 where they are securely fastened by conventional means. By pulling cables 112 from the proximal end of invagination device 90, arms 106 are caused to open as shown in FIG. 20. The amount arms 106 are opened is controlled by the distance cables 112 are withdrawn from invagination device 90.

Cables 112 may be independently actuable by providing cable withdrawal mechanisms for each cable. Such withdrawal mechanisms can include finger loops, triggers, actuation handles, or any other remotely operated device which can be attached to a cable for withdrawal. Alternatively, cables 112 may be actuated by a single withdrawal mechanism which is attached to all of the cables.

Figure 21:
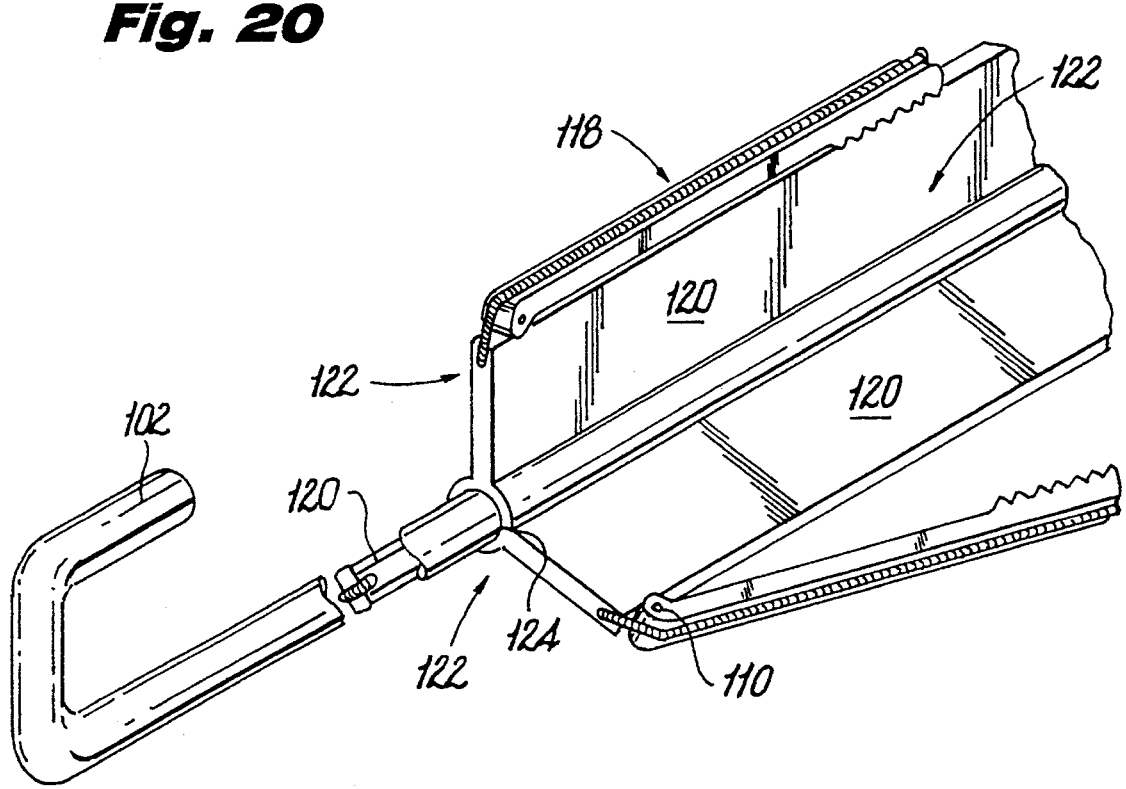
FIG. 21 is a perspective view of an invagination device in accordance with another preferred embodiment of the present invention.

Another preferred embodiment of the invagination device for an endoscopic fundoplication system according to the present invention is shown in FIG. 21. The invagination device 118 is formed by the intersection of walls 120. The intersection of an adjacent pair of walls forms stapler channels 122. As in the previous embodiment, endoscope 102 passes through a central guide channel 124. The remaining elements of invagination device 118 are substantially similar to those of invagination device 90 (FIG. 19–20).

Referring to FIGS. 22–28 a method of using the endoscopic fundoplication system of FIG. 19 will be described. Before invagination device 90 is inserted, the stomach is optionally insufflated according to known procedures. Invagination device 90 with endoscope 102 positioned in channel 100 is inserted into the esophagus and carefully advanced into the stomach, slightly beyond the site of the gastroesophageal junction. Clamping members 104 are biased towards body portion 92 by any suitable means, i.e., springs.

Figure 23:
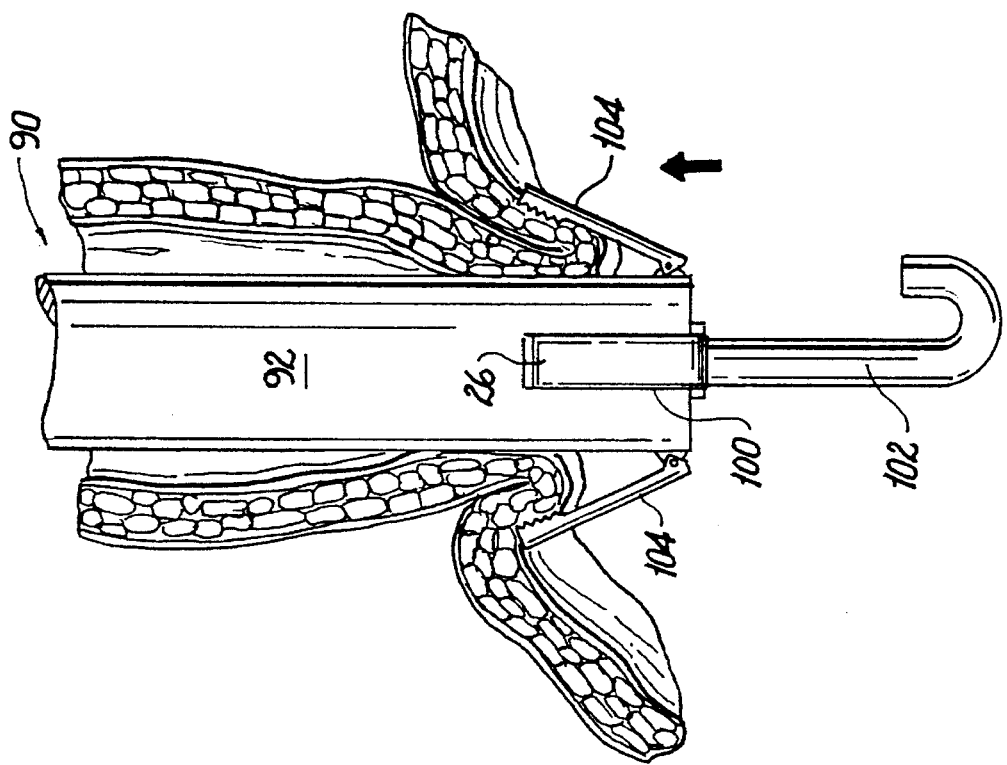
FIG. 23 is a view similar to that of FIG. 22 showing the arms of the invagination device of the present invention engaging stomach tissue at the gastroesophageal junction.
Figure 22:
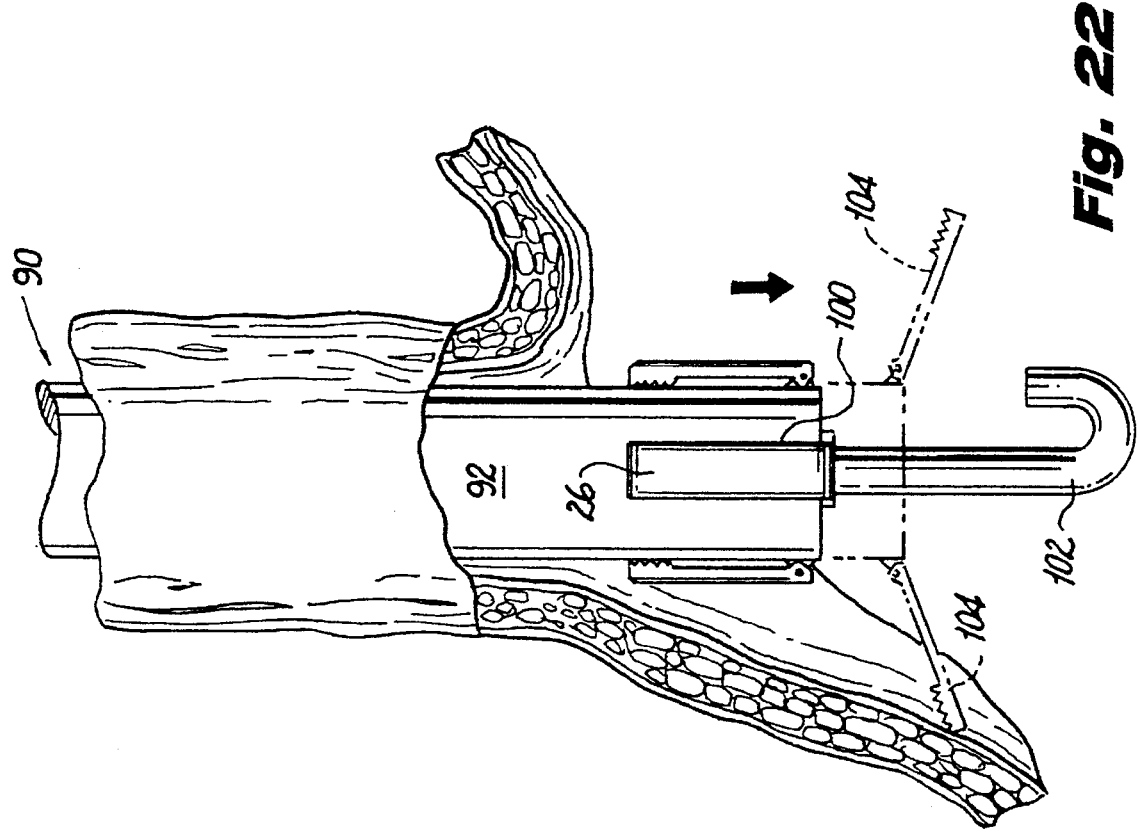
FIG. 22 is a partial cross-sectional view of the invagination device of FIG. 19 positioned within the stomach.

After assuring correct positioning of invagination device 90, clamping members 104 are opened, either simultaneously or sequentially, through retraction of cables 112 (FIG. 19). Invagination device 90 is partially withdrawn proximally into the esophagus as cables 112 are gradually released (FIG. 23). Stomach and esophageal tissue adjacent the gastroesophageal junction are captured by clamping members 104 and securely held against body portion 92 of invagination device 90 (FIG. 24).

Figure 25:
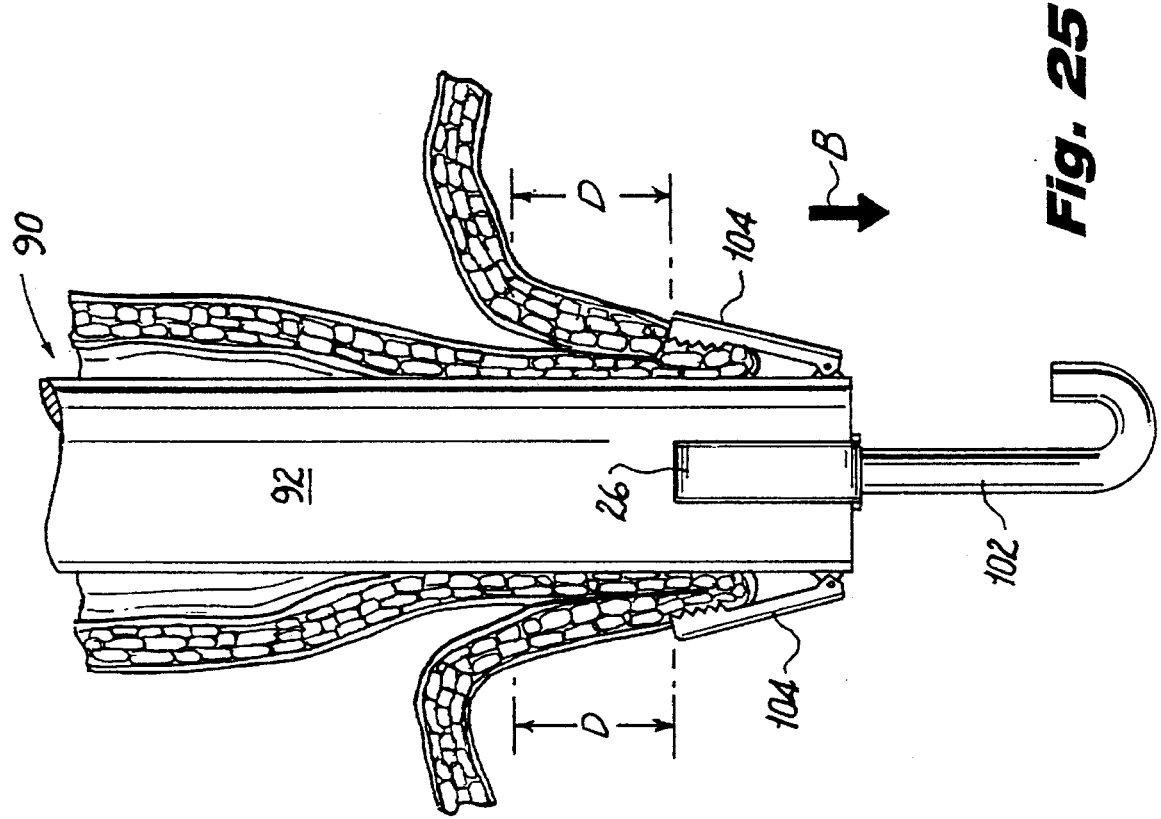
FIG. 25 is a view similar to that of FIG. 24 illustrating the invagination of the gastroesophageal junction.
Figure 24:
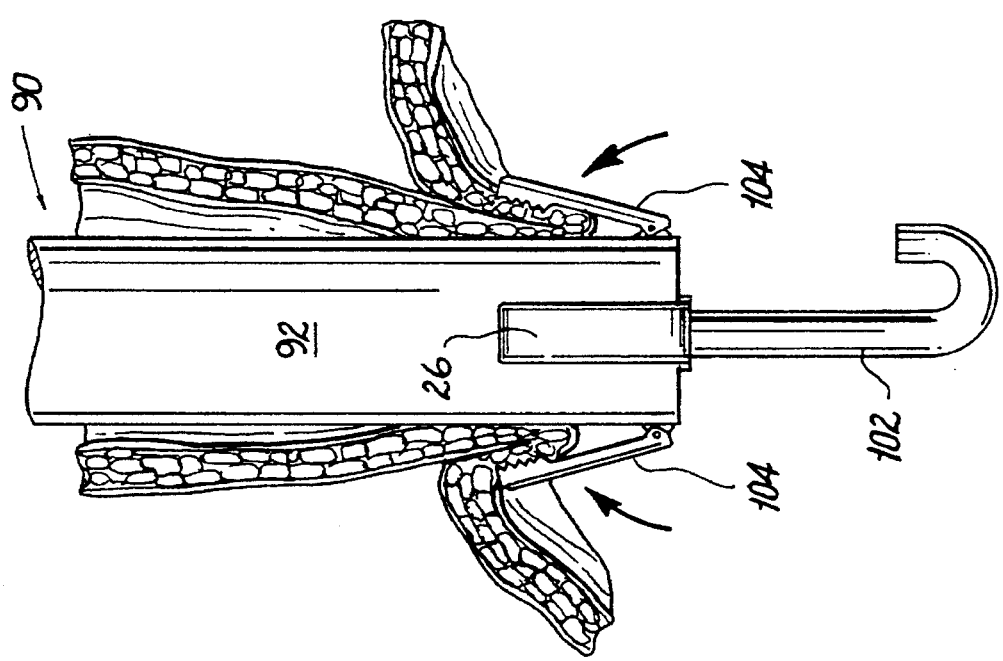
FIG. 24 is a view similar to that of FIG. 23 with stomach and esophageal tissue clamped by the invagination device of the present invention.
Figure 29:
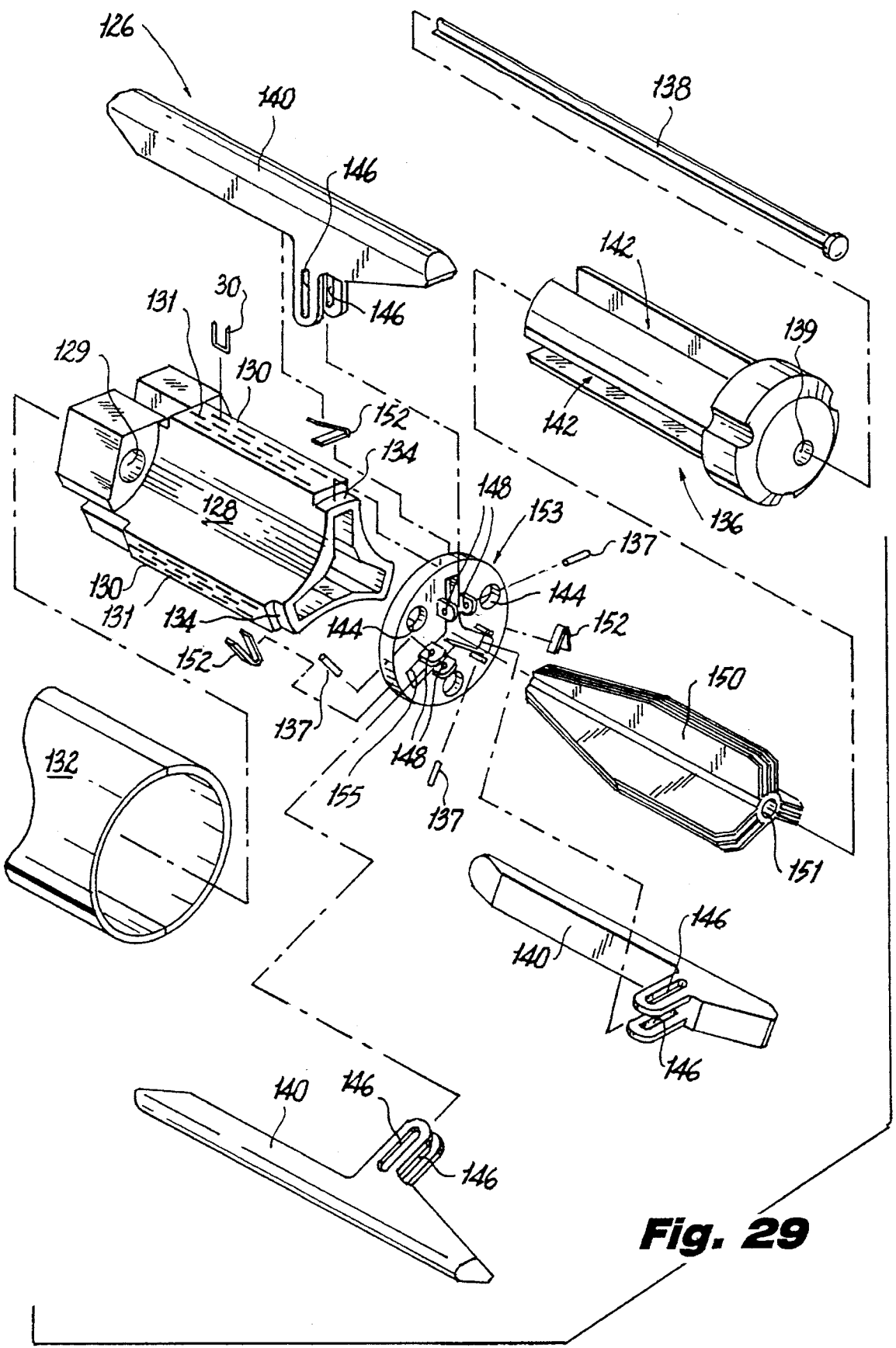
FIG. 29 is an exploded perspective view of a stapling device according to another preferred embodiment of the present invention.

Referring to FIGS. 24–25, with the tissue securely clamped, invagination device 90 is advanced in a distal direction "B" into the stomach to cause invagination of the esophagus into the stomach and involution of the stomach about the lower esophagus. The invagination is of a predetermined distance "D" to causing stomach portions to contact body portion 92 of invagination device 90.

Referring to FIGS. 26–27, fastening instrument 10 is inserted into one of guide channels 94 with anvil 26 in a closed position. Like invagination device 90, fastening instrument 10 is inserted beyond the gastroesophageal junction to allow anvil 26 to be pivoted open and tissue to be captured (FIG. 26). After opening, fastening instrument 10 is retracted proximally, FIG. 27, capturing tissue until cartridge 24 (FIG. 3) is aligned with slot 96 (FIG. 19). Anvil 26 is then closed, clamping tissue to be fastened in a manner similar to that described above. Staple ejectors 28 (FIG. 3) are then actuated, driving staples through clamped tissue and formed against the anvil (FIG. 5).

After firing, fastening instrument 10 is opened, advanced into the stomach, closed, and withdrawn from guide channel 94 (FIG. 19). If desired, the stapling process is repeated in one or more of the remaining guide channels 94 to form additional rows of staples. Alternately, invagination device 90 can be repositioned and the stapler placed through the stapler guide channel.

Following stapling, clamping members 104 are opened to release the tissue. Invagination device 90 is then advanced towards the stomach so that clamping members 104 may be closed without capturing any tissue. Invagination device 90 is then removed from the esophagus at the completion of the procedure (FIG. 28).

Figure 30:
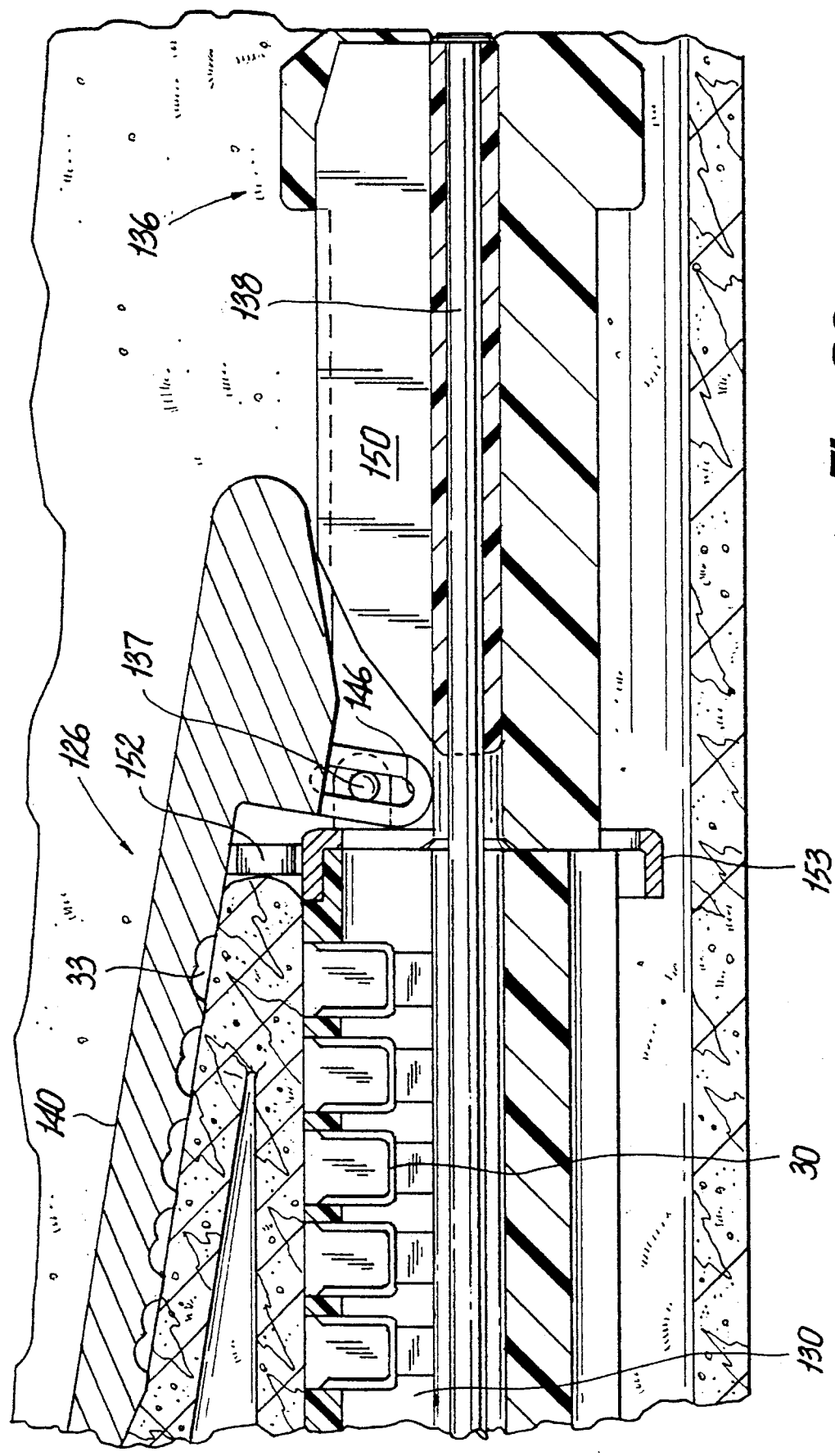
FIG. 30 is an enlarged partial cross-sectional side view of the stapling device of FIG. 29 engaging tissue with an anvil partially open.
Figure 31:
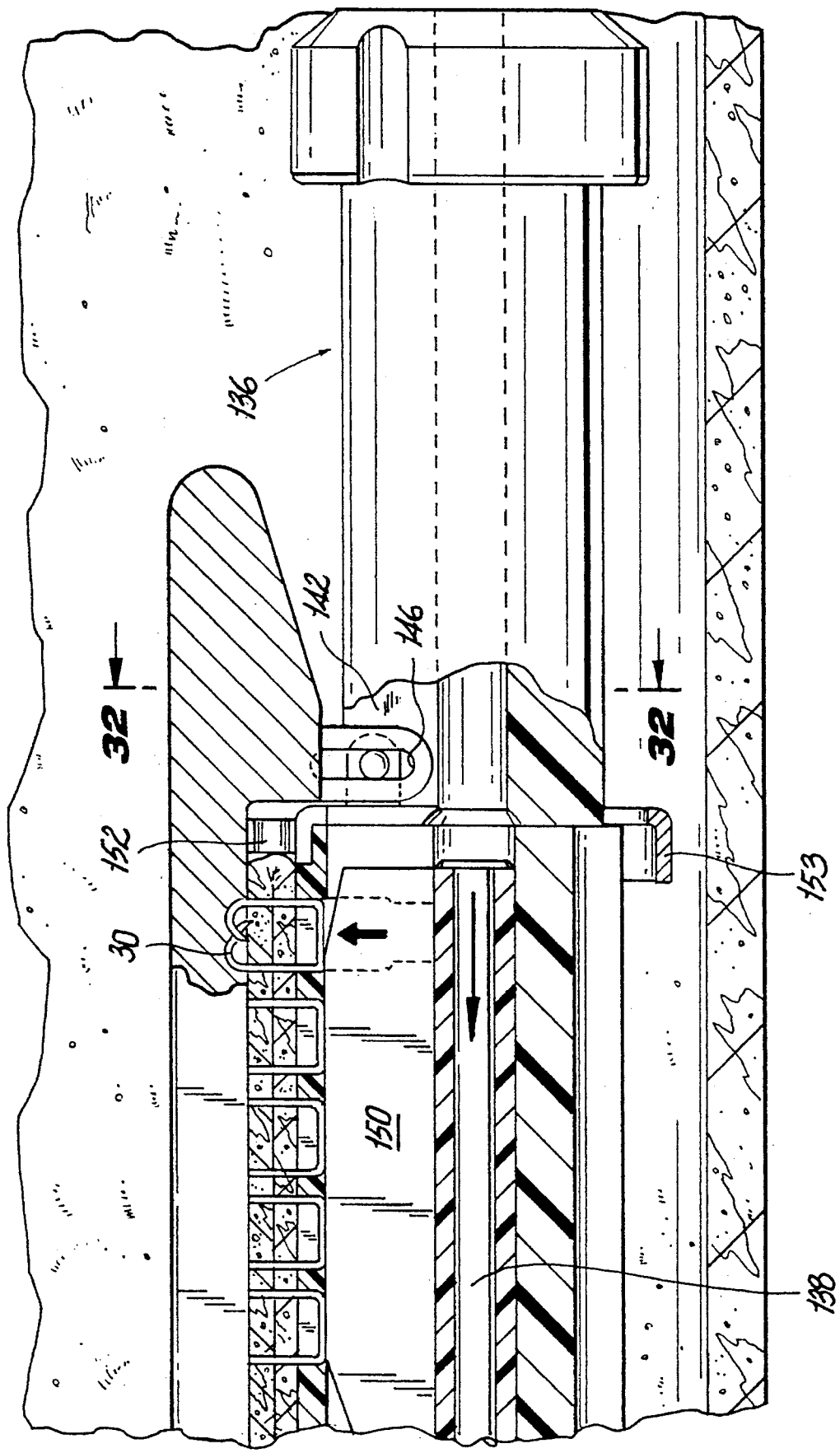
FIG. 31 is a view similar to that of FIG. 30 showing the device after staples have been fired.
Figure 32:
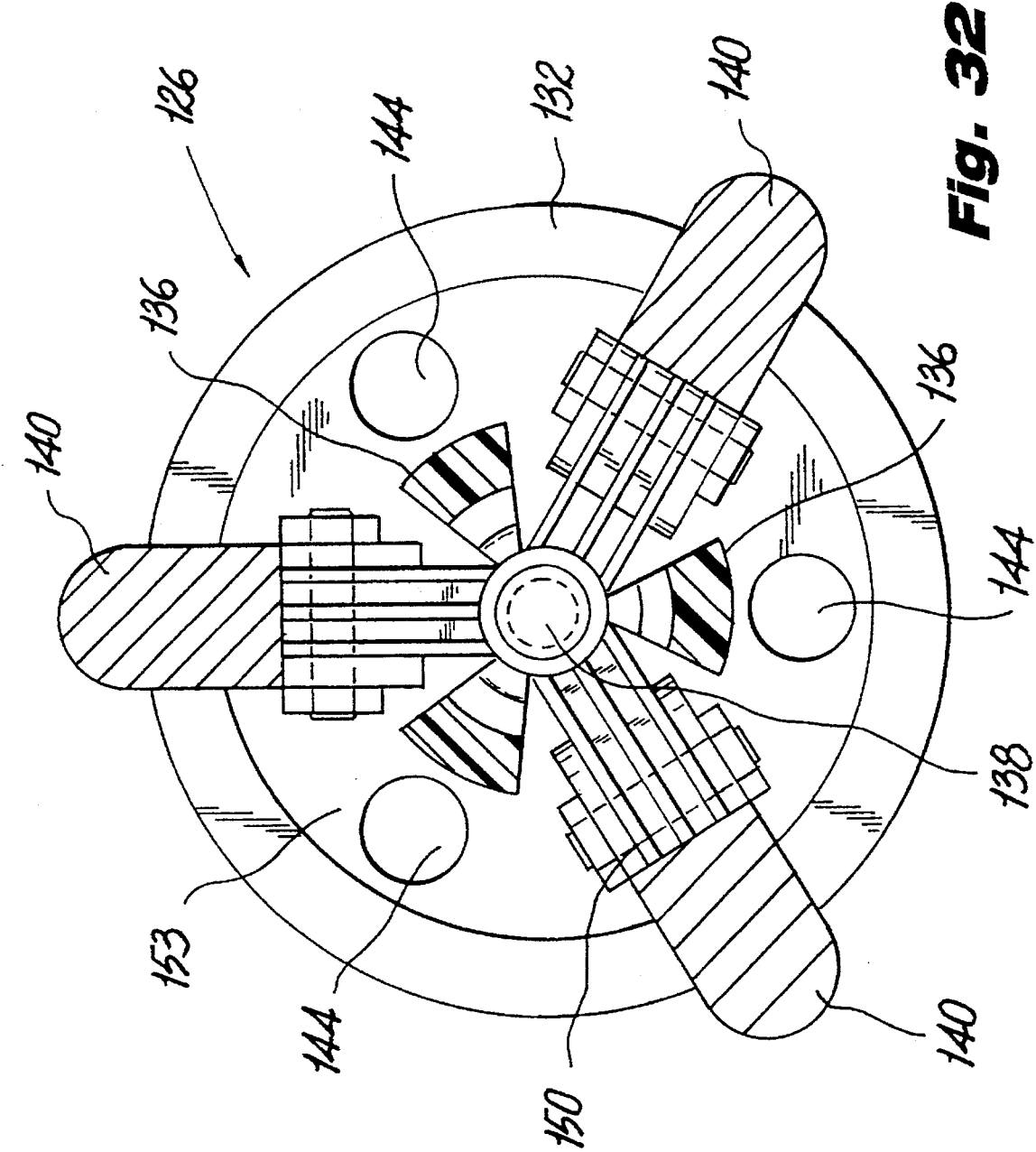
FIG. 32 is a view of the distal end of the stapling device of FIG. 29.

Another embodiment of a fastening instrument is shown in FIGS. 29–32. Fastening instrument 126 includes staple cartridge 128 having three tissue contacting surfaces 130. Each tissue contacting surface contains rows of staples 30 disposed in staple receiving slots 131. Each surface 130 is located in a different plane and spaced approximately 120° apart from one another. The proximal end of cartridge 128 is disposed within outer sheath 132 and has three holes 129 for passage of an endoscope or other instrumentation. Disk member 153 is secured to the distal end of cartridge 128 by any suitable means, i.e., pins, screws, glue, weld, or the like. As shown in FIGS. 30 and 31, disk member 153 can sit on shelf portions 134 of cartridge 128. Disk member 153 includes holes 144, which correspond to holes 129 in body portion 128, and projections 148, the purpose of which is discussed below.

Cap member 136 has slots 142 for passage of staple ejector 150 and bore 134 for passage of rod 138. Cap member 136 is connected to the distal end of disk member 153 by any suitable means. Rod 138 passes through cap bore 139 and center bore 151 in triple staple ejector 150. Fastening instrument 126 further includes anvils 140 having pivot slots 146. Anvils 140 are pivotally connected to disk 153 by pivot pins 137 (FIG. 30) placed through pivot slots 146 and projections 148.

Referring to FIGS. 29–32, the operation of fastening instrument 126 will be described wherein one of the three staple cartridges 130 is illustrative of the functioning of all three of staple cartridges 130. Tissue to be joined is securely clamped and invaginated by an invagination device. Fastening instrument 126 is transorally inserted through the esophagus into the stomach. Anvils 140 are initially biased open by spring members 152 and triple staple ejector 150 is initially disposed distal of cartridge 128 in cap member 136. with reference to FIG. 30, proximal movement of rod 138 causes a proximal portion of staple ejector 150 to cam against a distal portion of anvil 146. This camming action overcomes the biasing forge of spring 152 and the anvil is brought into alignment with surface 130 of cartridge 128. Pivot slots 146 allow anvil 140 to adjust to the thickness of tissue clamped between anvil 140 and staple cartridge 130.

With tissue firmly clamped between anvil 140 and surface 130 triple staple ejector 150 is further retracted, i.e., by a trigger member (not shown) operatively associated with rod 138. In this manner, triple staple ejector 150 drives staples 30 into staple forming depressions 33 where staples 30 are deformed. Upon completion of the stapling operation, anvils 140 are biased open by springs 152. Fastening instrument 126 can then be withdrawn.

It will be understood that various modifications may be made to the embodiments disclosed herein. Therefore, the above description should not be construed as limiting but merely as exemplification of preferred embodiments. Those skilled in the art will envision other modifications within the scope and spirit of the claims appended hereto.

What is claimed is:

1. A surgical stapler comprising:

a staple carrying cartridge having at least two rows of staples;

and first and second independently actuable staple ejecting members longitudinally slidably disposed within the staple carrying cartridge, the first staple ejecting member movable from a first position to a second position to fire at least one said rows of staples while the second staple ejecting member remains in the cartridge.

2. A surgical stapler comprising:

a frame member having a stationary handgrip and a movable trigger;

an elongated portion extending distally from the frame member;

a staple carrying cartridge disposed at a distal end of the elongated portion, the staple carrying member having at least two staple pushing members longitudinally slidably disposed therein;

a clutch assembly disposed within the frame member, the clutch assembly having at least two rotatable members capable of independent rotation; and at least two elongate firing members having proximal and distal ends, each firing member proximal end being secured to one of the at least two rotatable members and each firing member distal end being secured to one of the at least two staple pushing members;

wherein a first movement of the trigger causes rotation of one of the rotatable members, thereby causing longitudinal movement of one of the staple pushing members and a second, subsequent movement of the trigger causes rotation of another of the rotatable members, thereby causing movement of another of the staple pushing members.

3. A staple carrying cartridge comprising:

a tissue contacting surface having a plurality of staple receiving slots;

a plurality of staples disposed within the staple receiving slots;

a staple ejecting member longitudinally slidably disposed within the staple carrying cartridge; and a tissue traumatizing member vertically movable from a first position below the tissue contacting surface, to a second position above the tissue contacting surface;

wherein longitudinal movement of the staple ejecting member causes the tissue traumatizing member to move from the first position to the second position.

4. A fastener carrying cartridge comprising first and second tissue contacting surfaces, each tissue contacting surface defining a plane and having a parallel row of fastener receiving slots, and at least one fastener ejecting member slidably disposed at an angle to one another within the faster carrying cartridge for sequentially ejecting at least one said first and second rows of fasteners, wherein said first tissue contacting surface is disposed at an angle with said second tissue contacting surface.

5. In combination, a surgical stapling device and guide therefore, comprising a) a surgical stapler having:
  i) a cartridge frame;
  ii) a staple cartridge disposed in the cartridge frame; and
  iii) an anvil pivotally mounted with respect to the cartridge frame; and b) a surgical stapler guiding device having:
  i) an elongate member having a distal end and a proximal end;
  ii) at least one longitudinal channel disposed between the elongate member distal and proximal ends; and
  iii) a slot extending along at least a portion of in the exterior of the elongate member;

wherein the cartridge frame, staple cartridge and anvil of the surgical stapler are insertable into the proximal end of the longitudinal channel of the surgical stapler guiding device and the slot is adapted to permit the anvil to pass therethrough wherein the anvil is pivotable from a first position within the stapler guiding device to a second position wherein the anvil is at least partially disposed exterior to the stapler guiding device.

6. A method of placing a surgical fastener into body tissue comprising the steps of:

a) providing a surgical fastening device having:

i) a cartridge frame having proximal and distal portions;
ii) fastener carrying cartridge at least partially disposed in the frame; and
iii) an anvil member pivotally secured to the frame;

b) inserting the fastening device into the mouth of a patient;

c) guiding the fastening device through the patient's esophagus;

d) invaginating at least a portion of the esophagus into the stomach prior to the step of applying the at least one fastener, wherein the stem of invagination is accomplished by providing an invagination device for gripping the gastroesogeal junction and (e) applying at least one fastener to esophageal tissue, wherein the surgical fastening device is insertable within the invagination device and the step of applying the at least one fastener is preceded by a step of inserting the fastening device within invagination device.

7. The method of claim 6, wherein the step of invaginating comprises the step of gripping a portion of the gastroesophageal junction.

8. The method of claim 6, wherein the step of invaginating is at least partially accomplished by clamping tissue between the fastener carrying cartridge and the anvil member.

9. The method of claim 6, wherein the step of providing the invagination device includes providing the device with at least one movable member adapted to grip the gastroesophageal junction.

10. The method of claim 6, wherein the anvil member is pivotally secured to the distal end of the frame and the step of invaginating is at least partially accomplished by:

a) advancing the fastening device at least partially past the gastroesophageal junction;

b) positioning tissue between the anvil member and the fastener carrying cartridge;

c) gripping the positioned tissue; and d) advancing the fastening device and gripped tissue towards the patient's stomach.

11. The method of claim 6, further comprising the step of applying additional fasteners at different location in the esophagus.

12. The method of claim 6, wherein the surgical fasteners are staples and the step of applying comprises ejecting the staples from the fastener carrying cartridge and forming the staples against the anvil member.

13. A method of firing rows of staples from a surgical stapler, the method comprising the steps of:

a) providing a staple carrying cartridge having first and second parallel rows of staples;

b) providing an anvil member;

c) disposing the anvil member adjacent the staple carrying cartridge such that staples ejected from the cartridge can be formed against the anvil member;

d) ejecting the first row of staples from the staple carrying cartridge, thereby forming the staples against the anvil member;

e) maintaining the anvil member adjacent the staple carrying cartridge; and f) ejecting the second row of staples from the staple cartridge.

* * * * *

UNITED STATES PATENT AND TRADEMARK OFFICE
CERTIFICATE OF CORRECTION

PATENT NO. : 5,571,116
DATED : November 5, 1996
INVENTOR(S) : Henry Bolanos, Jeffrey J. Blewett, Timothy O. Van Leeuwen It is certified that error appears in the above-indentified patent and that said Letters Patent is hereby corrected as shown below:

On title page, item [22] should read as follows:

Filed: November 2, 1994

Signed and Sealed this

Fourth Day of November, 1997

Attest:

BRUCE LEHMAN

Attesting Officer     Commissioner of Patents and Trademarks